United States Patent
Vogt et al.

(10) Patent No.: US 11,751,885 B2
(45) Date of Patent: Sep. 12, 2023

(54) PRESSURIZED GAS ENGINE AND METHOD OF OPERATING A PRESSURIZED GAS ENGINE

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 437 days.

(21) Appl. No.: 17/068,264

(22) Filed: Oct. 12, 2020

(65) Prior Publication Data
US 2021/0137548 A1 May 13, 2021

(30) Foreign Application Priority Data
Nov. 13, 2019 (EP) .................................. 19208962

(51) Int. Cl.
*A61B 17/16* (2006.01)
*A61B 17/14* (2006.01)
(Continued)

(52) U.S. Cl.
CPC .......... *A61B 17/1628* (2013.01); *A61B 17/14* (2013.01); *A61B 17/1659* (2013.01);
(Continued)

(58) Field of Classification Search
CPC .......... A61B 2017/00544; A61B 17/14; A61B 17/142; A61B 17/1628; A61B 17/1659; F15B 11/06; F15B 11/076; F15B 11/15
See application file for complete search history.

(56) References Cited

U.S. PATENT DOCUMENTS 2,000,890 A  5/1935  Hueber et al.
2,601,848 A  7/1952  Dahlberg
(Continued)

FOREIGN PATENT DOCUMENTS

DE  1476673 A1  4/1970
DE  2428853 A1  1/1976
(Continued)

OTHER PUBLICATIONS

Notice of Reasons for Rejection dated Oct. 12, 2021 by the Japanese Patent Office for counterpart Japanese Patent Application No. 2020-168993 (with English translation).

*Primary Examiner* — Larry E Waggle, Jr.
(74) *Attorney, Agent, or Firm* — Dicke, Billig & Czaja, PLLC

(57) ABSTRACT

A compressed gas motor. The motor has a port and a hollow cylinder delimited by a wall with a ventilation opening, a rear closure, and a plunger axially movable in the cylinder. The plunger divides the cylinder into front and back chambers. The ventilation opening is periodically opened towards the back chamber during operation of the motor by movement of the plunger. A compression spring in the front chamber urges the plunger towards the rear closure and/or a tension spring in the back chamber draws the plunger towards the rear closure so that the back chamber is closed relative to the ventilation opening by the plunger and the back chamber is connected with the port when the same pressure prevails in the front and back chambers. The motor can be used in surgical drive systems, medical lavage systems and medical devices. Also disclosed is a method for operating the motor.

24 Claims, 16 Drawing Sheets

(51) Int. Cl.
*F15B 11/076* (2006.01)
*F15B 11/15* (2006.01)
*A61B 17/3203* (2006.01)
*F15B 15/14* (2006.01)
*A61B 17/00* (2006.01)
*F15B 15/17* (2006.01)

(52) U.S. Cl.
CPC ........ *A61B 17/3203* (2013.01); *F15B 11/076* (2013.01); *F15B 11/15* (2013.01); *F15B 15/1476* (2013.01); *A61B 2017/00398* (2013.01); *A61B 2017/00544* (2013.01); *A61B 2017/32035* (2013.01); *F15B 15/17* (2013.01)

(56) References Cited

U.S. PATENT DOCUMENTS

| | | | |
|---|---|---|---|
| 3,327,635 A | 6/1967 | Sachnik | |
| 3,731,662 A * | 5/1973 | Fandrich | F01B 11/007 123/50 B |
| 4,278,078 A | 7/1981 | Smith | |
| 4,583,531 A | 4/1986 | Mattchen | |
| 4,993,924 A | 2/1991 | Mukumoto et al. | |
| 5,542,918 A | 8/1996 | Atkinson | |
| 5,554,011 A | 9/1996 | Bales et al. | |
| 5,924,602 A | 7/1999 | Brown et al. | |
| 6,736,292 B2 | 5/2004 | Grach et al. | |
| 6,758,842 B2 * | 7/2004 | Irion | A61M 1/85 606/171 |
| 6,923,348 B2 | 8/2005 | Grach et al. | |
| 8,292,909 B1 | 10/2012 | Dubois et al. | |
| 9,861,770 B2 * | 1/2018 | Vogt | A61M 1/81 |
| 9,964,100 B2 * | 5/2018 | Vogt | F04B 7/02 |
| 2003/0164387 A1 | 9/2003 | Grach et al. | |
| 2005/0084395 A1 | 4/2005 | Kang | |
| 2013/0180396 A1 | 7/2013 | Vogt et al. | |

FOREIGN PATENT DOCUMENTS

| | | |
|---|---|---|
| DE | 2816617 C2 | 12/1985 |
| DE | 3724110 A1 | 2/1989 |
| DE | 102010046057 B3 | 1/2012 |
| DE | 102011018708 A1 | 10/2012 |
| EP | 2873856 A1 | 5/2015 |
| EP | 2910270 A1 | 8/2015 |
| EP | 2939699 B1 | 12/2018 |
| JP | H01-015922 | 5/1989 |
| JP | 2013-539668 | 10/2013 |
| WO | 2012/038003 A1 | 3/2012 |

* cited by examiner

PRESSURIZED GAS ENGINE AND METHOD OF OPERATING A PRESSURIZED GAS ENGINE

RELATED APPLICATION

This application claims the benefit of priority to European Patent Application Number EP 19208962.1, filed on Nov. 13, 2019, the contents of which are incorporated in this application by reference.

TECHNICAL FIELD

The present disclosure relates generally to pressurized or compressed gas engines or motors and, more particularly, to such engines as used in surgical drive systems, medical lavage systems and medical devices.

BACKGROUND OF THE DISCLOSURE

In orthopedic surgery, a certain degree of septic revisions of joint endoprostheses infected with microorganisms must unfortunately be undertaken. In this process, the infected joint endoprostheses are explanted and the infected or necrotic tissue removed. This removal of infected/necrotic tissue is known as debridement. The debridement may be carried out by wound rinsing with "lavage" systems and by cutting out, rasping, sawing and also brushing. After debridement, the devices used for debriding are contaminated with tissue residue and with microbial microorganisms. If they are to be reused, these instruments have to be thoroughly cleaned and then sterilized. When doing so, medical personnel have to protect themselves from contamination or infection by transfer of microbial microorganisms during cleaning operations. It is therefore desirable to be able to provide an inexpensive device with a motor drive for rasping, sawing and brushing and for lavaging for the purpose of septic revision, which device could be discarded together with the usual surgical waste after a single use without complex and possibly hazardous cleaning steps. It would then be sensible, particularly for resource and environmental protection but also for reasons of cost, if no batteries, storage batteries or electric motors were necessary for the drive.

In medicine, drive devices operated with compressed air and with electrical energy are currently known. The drive systems based on compressed air generally contain lamellae air motors. What is problematic is that non-sterile compressed air is supplied by hose and after the drive of the motor, the expanded, non-sterile air has to be removed from the operating room in a separate hose. Coaxial hose systems are often used for this purpose. Drives operated with compressed air have largely been replaced by electrically operated drive systems. These drive systems have electric motors with transmissions and conventionally use storage batteries as their energy source. The electrically operated drive systems contain copper and further heavy metals.

In lavage systems, spray jets of rinsing liquids are generated which impact on the areas of tissue to be cleaned and exert a mechanical cleaning action on these areas of tissue. Pulsed lavage systems have long been known, for example from U.S. Pat. Nos. 4,583,531, 4,278,078 and 5,542,918.

U.S. Pat. No. 9,861,770 proposes a vacuum motor in which a spiral spring is tensioned by the action of a vacuum on a plunger. At the end of the tensioning process, momentum is imparted to a valve plunger, which opens up ventilation openings and briefly closes the vacuum openings. The tensioned spiral spring may relax and drives the plunger back to the starting position and thus drives a pump plunger connected thereto. This results in a periodic, linear, oscillating pump motion, which is driven by the spiral spring, wherein tensioning of the spiral spring proceeds by a pressure difference. A disadvantage of this design is that the vacuum motor has many parts and above all at least three parts movable relative to one another plus the spiral spring. With all the parts movable within the vacuum motor there is a risk of these jamming or overheating due to friction at high frequencies. An even simpler vacuum motor would be desirable.

U.S. Pat. No. 5,542,918 discloses a fluid pump for a lavage system which is driven by a vacuum and in which a diaphragm is driven by a hollow, linearly movable, resiliently mounted plunger, in which a likewise resiliently mounted valve plunger is arranged for opening and closing a gas inlet for supplying air. The system has the disadvantage that, in the open state, the valve element can only provide a small free flow cross-section. Consequently, the power that can be generated by the pump is limited and the risk arises of a dead center, from which the pump does not start again by itself. In addition, the lack of guidance of the valve plunger may lead to lateral movements of the valve plunger and thereby to irregular plunger oscillations.

A further pump for generating pulsed liquid jets is known from DE 102011018708A1. Here, too, a plunger vibrator acts on a diaphragm, which is used as a pump. The plunger of the plunger vibrator is complex in its construction. In addition, the dimensions have to be very precisely adhered to during construction in order to ensure trouble-free operation.

U.S. Patent Application Publication No. 2005/0084395 discloses a vacuum-driven lavage system which operates by way of two cylinders. In the cylinders, two mutually coupled plungers are driven by the vacuum. This construction is also very complex to produce due to the plungers being coupled together via joints.

U.S. Pat. No. 8,292,909 describes a double-acting vacuum motor. In this vacuum motor, power is transferred to a valve plunger by a bi-stable coupling element at the end of the forward and return movements of the working plunger, whereby the latter transfers from one switching state to a second switching state. This way, the valve plunger remains in a defined switching state during the movement of the working plunger. The switching state of the valve plunger is thus defined by the respective end position of the working plunger. This concept also requires a major manufacturing and assembly effort.

The forces that can be achieved with the vacuum motors are sufficient for spraying liquids. To drive saws, rasps and brushes, however, greater drive forces are needed.

The use of compressed gas motors for driving surgical tools is known. In this case, compressed air turbines are primarily used, in addition to lamellae air motors. The expanded air is generally recirculated with a special line, because the used compressed air is not sterile. After each use, reusable surgical compressed gas motors have to be cleaned and sterilized or at least disinfected. In the case of septic operations, the surgical instruments used and also the drive devices are naturally subjected to massive microbial contamination. Cleaning and preparation are complex and a health hazard. Furthermore, validation of both cleaning and sterilization is very complicated in the case of medical drive systems and is associated with high costs. It is therefore desirable, instead of reusable surgical drive devices, to develop drive devices for single use which may be discarded in an environmentally friendly manner after use by burning together with the infectious clinical waste.

When using compressed air-driven lavage systems, however, a double hose system has to be used, in which the non-sterile compressed air is supplied in one hose and a second hose is used with which the at least partly expanded non-sterile air is removed after drive of the compressed air motor. In systems driven with compressed air or another compressed gas, a compressed gas motor is conventionally used for drive purposes.

Compressed gas motors belong to the group of gas expansion motors. This means that the drive is accomplished by expansion (in particular by adiabatic expansion) of a pressurized gas. Conventional gas expansion motors/compressed gas motors may be subdivided into lamellae air motors, double helical wheel type air motors, compressed air turbines and plunger motors. In the case of the known plunger motors, inlet and outlet valves are used to control the inlet of compressed gas and outlet of the expanded gas. Slide gates are also used to control the inlet and outlet instead of valves. Most previous compressed gas motors are made substantially of steel and are intended for long-term use.

Such a compressed gas motor is known from International Patent Application Publication WO 2012/038003A1. The compressed gas motor described therein has a two-part plunger with an interspace and a passage through one of the plunger parts. This means the motor is of particularly simple and inexpensive construction. A compressed gas motor for a spray can is known from DE 3724110A1. A reciprocating pump driven with compressed gas is known from U.S. Pat. No. 4,993,924. A compressed gas motor for a lavage system is known from EP 2873856A1. In this compressed gas motor, a control plunger is moved by a working plunger via a pusher element and a gas inlet opening and a gas outlet opening are periodically opened and closed thereby when the compressed gas motor is in operation. A compressed gas motor with a plunger system is further known from DE 102010046057B3.

DE 2816617C2 discloses a compressed air motor with a double-acting plunger, in which the compressed air supply is controlled via separate slide gates. Similarly operating compressed air motors are described in documents DE 2428853C3, DE 1476673A1, U.S. Pat. Nos. 2,601,848 and 2,000,890.

There is always a desire for a motor of more inexpensive construction. There is also a need to provide a motor which can be operated with a higher frequency and/or a greater power.

U.S. Pat. No. 5,554,011 discloses a pump with a compressed gas motor, in which a valve element is controlled by the movement of a diaphragm. The work at the diaphragm is performed by the changing gas pressure, thereby driving the pump. The construction of this compressed gas motor is relatively effort-intensive and the diaphragm and the necessary clamping of the diaphragm in compressed gas motors of this type of construction may lead to different oscillatory characteristics. In addition, in the case of the valve element the risk arises of a dead center, from which the compressed gas motor can no longer continue by itself.

European Patent No. EP 2910270 B1 and U.S. Pat. No. 9,861,770 describe a compressed gas motor for driving a pump for a lavage system. The compressed gas motor consists of a working plunger movable axially in a cavity and a return element arranged therebehind. The working plunger has a pusher element, which moves a control plunger when in operation. The control plunger is a hollow cylinder and may conceal a gas outlet opening and a gas inlet opening by way of its closed circumferential surface. A vacuum source, such as for example a vacuum pump, is connected to the gas outlet opening. This means that when the motor is operated the gas outlet opening and the gas inlet opening are periodically concealed. When the gas outlet opening is open, the air is sucked out of the compressed gas motor, wherein the working plunger is moved against the return element. The feed air opening is simultaneously closed by the control plunger. The return element is tensioned. Then the pusher element imparts momentum to the control plunger. The control plunger moves away from the working plunger and opens the gas inlet opening and simultaneously closes the gas outlet opening. The vacuum breaks down and the return element moves the working plunger into its starting position. In the process, the pusher imparts momentum to the control plunger. The control plunger moves in the direction of the working plunger. The gas inlet opening is closed by the circumferential surface of the control plunger and the gas outlet opening is opened. Then the cycle starts again. This compressed gas motor is designed for high pulse rates of around 2,000 pulses per minute for operation of a pump for a lavage system. Stroke length is relatively short and amounts to between 2 and 5 mm. For brushing, rasping or sawing greater stroke lengths and smaller pulse rates are required. In addition, this construction is also complex. For manufacture of the compressed gas motor described in European Patent No. EP 2910270B1 and U.S. Pat. No. 9,861,770, components manufactured by plastic precision injection molding are needed. Assembly of these parts requires great care.

A further compressed gas motor for a lavage system is known from EP 2939699B1. In this compressed gas motor a vibration member is set in oscillation by a compressed gas passed through the compressed gas motor, with a plunger, which is mounted resiliently with a return element, wherein the vibration member and the plunger are positioned and mounted in such a way that the vibration member repeatedly impacts the plunger during oscillation and deflects it against the return element. A disadvantage of this device is that two parts movable relative to one another in the compressed gas motor hit one another and oscillation thus does not necessarily proceed as evenly as desired, such that the compressed gas motor is no longer readily usable for driving sawing, rasping or brushing. It is also possible to simplify the construction of the compressed gas motor even further and thereby reduce costs.

A compressed gas motor with a plunger exposed unilaterally to compressed air and a return spring was proposed in U.S. Pat. No. 5,924,602A. In this case, a valve is arranged in the plunger, which opens the space exposed to compressed air downstream of the plunger once an end position has been reached and releases the at least partially expanded compressed air into the surrounding environment. The valve mechanism is very complex and construction therefore effort-intensive.

A similarly acting compressed gas motor was described in U.S. Pat. Nos. 6,736,292 and 6,923,348. In this compressed gas motor a valve body is arranged axially and displaceably within a plunger. A peripheral groove is arranged in a drive cylinder. The plunger has two mutually spaced peripheral seals on a circumferential surface. An opening allowing passage of gas is arranged between the seals which is connected for passage of gas with the axially movable valve body. When the first and second seals of the plunger pass over the peripheral groove of the drive cylinder, compressed air flows through the groove below the second seal into the lateral opening of the plunger. In this way, the valve body is forced by the inflowing compressed air towards the base of the working cylinder. The valve opens a duct and the at least partly expanded compressed air may escape through this duct through the plunger into the surrounding atmosphere. Thereafter, the return spring pushes the plunger over the groove into the initial state, wherein the valve returns to its starting position and the entire process repeats providing compressed air is present at the compressed gas motor. Passing over the groove by the seals may pose problems. In particular, a change to the mode of operation of the compressed gas motor may arise due to heating resulting from friction. Furthermore, production and assembly of the parts of the compressed gas motor are complex.

SUMMARY OF THE DISCLOSURE

An object of the present invention thus consists of overcoming the disadvantages of the known devices. In particular, an object of the invention consists of developing a compressed gas motor which is relatively inexpensive and simple to manufacture, which operates reliably, is suitable for multipurpose use and achieves, by using the compressed air available in hospitals or a pressurized gas from a compressed gas cartridge, sufficient power to debride tissue and/or drive tools for surgical purposes. It is therefore also an object of the present invention to provide such surgical tools and lavage systems with such a compressed gas motor or a surgical drive system therewith. It is likewise an object of the present invention to provide a method for operating a compressed gas motor, wherein the method is intended to offer the advantages mentioned above in relation to the compressed gas motor.

Another object of the invention is to develop an extremely simplified, inexpensive compressed gas motor which can be driven with compressed air or with compressed gas and which generates an oscillating, linear motion. The compressed gas motor is intended to be simpler to construct and less expensive to manufacture than known compressed gas motors for driving a lavage system or for surgical tools. The compressed gas motor is intended to be suitable for driving tools such as rasps, saws or brushes, and for driving lavage systems and devices for debriding infected soft and bone tissue, which, as "disposable devices," are suitable for use only once for hygiene reasons. The compressed gas motor is intended to be sterilizable with ethylene oxide.

A further object of the invention consists of developing a maximally simplified compressed gas motor which is intended to drive a surgical drive system. The surgical drive system is intended for single use. The compressed gas motor is designed to consist of as few parts as possible and to be manufactured with minimal production effort. As far as possible, the compressed gas motor contains no separate valves, no valve controls and also no slide gate controls. The compressed gas motor consists substantially of plastic injection moldings and is suitable for environmentally compatible disposal. It avoids the use of batteries and storage batteries and of electric motors. Furthermore, the compressed gas motor is able to drive conventional surgical saw blades and similar tools. The compressed gas motor can be driven with any desired compressed gases and in particular with compressed air. The compressed air motor starts reliably and irrespective of location without auxiliary devices.

The objects which form the basis of the present invention are achieved by a compressed gas motor including:
A) a hollow cylinder delimited by a cylinder jacket wall,
B) a rear closure at a rear base of the hollow cylinder,
C) a plunger which moves axially in the hollow cylinder and which is connected at a front end of the plunger with a drive rod which projects out of the hollow cylinder, wherein the plunger divides the hollow cylinder into two inner chambers, specifically into
D) a back inner chamber of the hollow cylinder being delimited by the plunger, the cylinder jacket wall of the hollow cylinder and the rear closure, and
E) a front inner chamber of the hollow cylinder being delimited by the plunger and the cylinder jacket wall of the hollow cylinder and a front base of the hollow cylinder,
F) at least one compressed gas port, which leads into the back inner chamber of the hollow cylinder,
G) at least one ventilation opening in the cylinder jacket wall of the hollow cylinder, whereby the back inner chamber of the hollow cylinder is connected or connectable for passage of gas with the surrounding atmosphere during operation of the compressed gas motor, wherein the at least one ventilation opening is periodically openable towards the back inner chamber by the axially movable plunger during operation of the compressed gas motor by movement of the plunger,
H) at least one compression spring arranged in the front inner chamber, wherein the at least one compression spring rests during operation of the compressed gas motor at least temporarily against the front base of the hollow cylinder, and/or
I) at least one tension spring arranged in the back inner chamber, wherein the at least one tension spring is connected with the plunger and with the rear closure of the hollow cylinder, wherein
J) the at least one compression spring urges the plunger to such an extent towards the rear closure and/or the at least one tension spring draws the plunger to such an extent towards the rear closure that the back inner chamber of the hollow cylinder is closed relative to the at least one ventilation opening by the plunger and the back inner chamber is connected with the compressed gas port when the same pressure prevails in the front inner chamber of the hollow cylinder and in the back inner chamber of the hollow cylinder.

The at least one compression spring and/or the at least one tension spring may be embodied with in each case at least one spring element. Preferably, the at least one compression spring and/or the at least one tension spring is a spiral spring. The spring may also be a gas spring, a conical spring or another spring suitable for the purpose. Steel springs are particularly preferred in this case.

The at least one ventilation opening preferably connects the front inner chamber with the surroundings of the compressed gas motor if the at least one compression spring and/or the at least one tension spring has or have deflected the plunger fully in the direction of the rear closure when the back inner chamber is not exposed to gas pressure.

A cylinder or a cylindrical geometry for the purposes of the present invention, and in accordance with the general definition, is a body delimited by two parallel, planar, congruent surfaces (the rear base and the front base) and a circumferential surface or cylinder jacket surface, wherein the circumferential surface is formed of parallel straight lines. That is to say, the cylinder is formed by displacing a planar surface along a straight line which does not lie in this plane. The height and axis of the cylinder are produced by the spacing of the two planes in which lie the rear base and the front base.

If the straight lines are perpendicular to the bases, the cylinder is described as a right cylinder. It is preferred according to the invention for the hollow cylinder to have a right cylindrical geometry. Within the meaning of the present invention, a right circular cylinder is thus merely a particular instance of cylindrical geometry, though it is preferred due to the greater simplicity of manufacture.

In the present case, an axial direction is understood to mean the direction based on the cylinder axis of the hollow cylinder.

The axially movable plunger is preferably a rotationally symmetrical body, which is arranged in the hollow cylinder so as to be movable along its axis of symmetry.

The hollow cylinder may be delimited by two closed bases. The drive rod may project out of the hollow cylinder through one or two orifices in the front base. The drive rod may to this end by passed through a front closure of the hollow cylinder.

The cylinder jacket wall is preferably the wall which delimits the hollow cylinder at the cylinder jacket thereof. The cylinder jacket should be understood to mean the surface which extends parallel to the cylinder axis of the hollow cylinder and circumferentially around the cylinder axis of the hollow cylinder.

The front base of the hollow cylinder is arranged opposite the rear base of the hollow cylinder.

The plunger is not sealed with a seal against the hollow cylinder. In this way, the friction between the plunger and the hollow cylinder is reduced and a cooling air stream generated, on which the plunger can slide.

The plunger does not fit precisely in the hollow cylinder and/or the plunger exhibits play relative to the hollow cylinder, preferably at least 0.5 µm play, particularly preferably at least 1 µm play, very particularly preferably between 1 µm and 10 µm play.

Preferably, the at least one compressed gas port is arranged in the cylinder jacket wall of the hollow cylinder and/or in the rear closure, wherein particularly preferably the at least one compressed gas port is arranged in the cylinder jacket wall of the hollow cylinder. It is preferred according to the invention for the at least one compressed gas port to be a single compressed gas port.

Within the meaning of the present invention, the tension spring is also considered connected to the rear closure of the hollow cylinder when it is connected with the cylinder jacket wall of the hollow cylinder adjoining the rear closure, in the region of the back inner chamber of the hollow cylinder.

The front of the compressed gas motor is the side at which the drive rod exits the hollow cylinder. The drive rod can be used to drive a tool, such as for example a saw, a bone saw, a rasp or a brush. A diaphragm of a diaphragm pump may also be moved or driven with the drive rod.

The working surface of the plunger, at which the work is carried out by the compressed gas, is the rear of the plunger which delimits the front of the back inner chamber of the hollow cylinder. Accordingly, the back inner chamber of the hollow cylinder may be construed as the working chamber of the compressed gas motor.

The term "compressed gas" is understood to mean all pressurized gases which are at a higher pressure than the surrounding atmosphere. Compressed air with pressures greater than 3 bar or gas from a $CO_2$ cartridge is preferably used as the compressed gas.

In the case of compressed gas motors according to the invention, the compressed gas motor has a front closure of a front base of the hollow cylinder, wherein the front closure includes a hole, in particular a central axial hole, through which the drive rod is passed and wherein the front inner chamber of the hollow cylinder is delimited by the plunger, the internal wall of the hollow cylinder and the front closure, wherein the front closure preferably includes at least one opening allowing passage of gas.

The hollow cylinder is thereby closed to the outside. Only the movement of the drive rod stabilized by mounting in the front closure can be utilized or affected from the outside. Blockage of the plunger can thus be avoided or the probability thereof reduced.

The front closure preferably contains at least one opening allowing passage of gas. In this way, air can exit from the front inner chamber into the surrounding atmosphere on movement of the plunger towards the front closure. Overpressure in the front inner chamber, which would lead to a braking action, is thereby prevented. In addition, a gas stream or gas film between the back inner chamber and the front inner chamber can be maintained by a gap between the plunger and the cylinder jacket wall, over which stream or film the plunger can slide and which dissipates frictional heat. On return movement of the plunger towards the rear closure, air is sucked into the front inner chamber by the plunger movement. If no or excessively small openings allowing passage of gas are present in the front closure, the inflow of air into the front inner chamber is reduced or prevented. In this way, braking of the movement of the plunger and the drive rod may occur. It is additionally or alternatively possible to arrange at least one opening allowing passage of gas directly in front of the front closure in the cylinder jacket wall of the hollow cylinder.

Furthermore, the plunger divides the hollow cylinder into two inner chambers separate from another, namely the front inner chamber and the back inner chamber. Preferably, the plunger divides the hollow cylinder into two inner chambers separate from one another in a non-gas-tight manner.

In this way, it is ensured that the plunger can be accelerated towards the front inner chamber by a buildup of pressure in the back inner chamber.

A compressed gas line can be connected with the compressed gas port, such that the compressed gas line is connected with the back inner chamber of the hollow cylinder in a manner which allows passage of gas.

This way, compressed gas can be introduced through the compressed gas line into the back inner chamber in a simplified manner.

Furthermore, the drive rod is arranged parallel to the cylinder axis of the hollow cylinder, preferably on the cylinder axis of the hollow cylinder.

In this way, the movement of the drive rod is oriented to match the direction of the force acting due to the gas pressure. In this way, jamming and blockage of the plunger and energy losses on movement of the plunger in the hollow cylinder can be avoided.

For the same purpose, the plunger and the drive rod are arranged in the hollow cylinder in a linearly movable manner, in particular an axially movable manner based on an axis of symmetry of the plunger and/or of the drive rod.

Furthermore, the plunger, on introduction of a pressurized compressed gas through the at least one compressed gas port into the back inner chamber of the hollow cylinder, causes oscillating movement of the drive rod by periodic changing of the action of the compressed gas and of the surrounding atmosphere in the back inner chamber, wherein preferably the at least one compression spring and/or the at least one tension spring can be tensioned by the movement of the plunger towards the front base of the hollow cylinder, driven by the compressed gas, and the plunger can be urged by the tensioned at least one compression spring and/or the tensioned at least one tension spring towards the rear base when the back inner chamber is open to the surrounding atmosphere.

It is thereby ensured that the compressed gas motor runs constantly while the compressed gas is flowing through the compressed gas motor or the back inner chamber.

According to a preferred further development, the plunger has a diameter of greater than or equal to 20 mm, preferably of greater than or equal to 30 mm and particularly preferably of greater than or equal to 35 mm.

The diameter here relates to the dimension of the (preferably at least in places cylindrical) plunger perpendicular to the cylinder axis of the hollow cylinder.

These measures ensure that, with a conventional compressed gas or compressed air available in hospitals, sufficient power for medical tools may be provided as a drive.

A fastening element, in particular a thread, is arranged on the front of the at least one drive rod, by which fastening element a tool, such as a saw, a rasp or a brush, is fastened by a counter-fastening element matching the fastening element, in particular a counter-thread matching the thread, on the at least one drive rod.

In this way, the compressed gas motor can be used to drive different tools which can be fastened to the fastening element of the drive rod.

The drive rod is equipped with a fastening element for a tool. Saw blades, rasps, brushes and lavage attachments, which operate as pulsed pumps, can be connected as tools. It is furthermore possible to couple the drive rod to a transmission, which reshapes the linear oscillating movement of the drive rod into rotational motion.

Preferably, the cylinder jacket wall delimiting the hollow cylinder, the plunger, the rear closure and, where present, also a front closure, are made from a plastic material, in particular from a thermoplastic, preferably formed by injection molding.

In this way, the compressed gas motor can be provided as a relatively inexpensive single-use tool which can be hygienically discarded.

The at least one compression spring is a spiral spring, wherein the spiral spring encloses the drive rod, wherein preferably no tension spring is arranged in the back inner chamber.

In this way, the compressed gas motor is of particularly simple construction. At the same time, reliable functioning of the compressed gas motor is achieved. By arranging the spiral spring around the drive rod, the spiral spring is always guided and cannot deviate from the longitudinal axis. The spiral spring is preferably not fixed on the front closure and/or on the plunger. The spiral spring may alternatively also be fixed in the region of the front base or on the front closure and on the plunger, whereby the functionality of the compressed gas motor is not impaired, however, and also is not improved.

According to a particularly preferred embodiment of the present invention, a gap allowing passage of gas exists between the plunger and the cylinder jacket wall of the hollow cylinder, by which gap the back inner chamber and the front inner chamber are connected together for passage of gas, wherein the gap preferably has a cross-sectional area which amounts to less than 1% of the cross-sectional area of the hollow cylinder perpendicular to the cylinder axis, particularly preferably amounts to less than 0.5%, very particularly preferably less than 0.1% of the cross-sectional area of the hollow cylinder perpendicular to the cylinder axis.

It has surprisingly been found that a small gap between the plunger and the cylinder jacket wall of the hollow cylinder allows the plunger to slide on a gas film of the flowing compressed gas (as a type of air cushion) and so is conducive to frictionless movability of the plunger in the hollow cylinder. Friction between the plunger moving in the hollow cylinder and the outer cylinder jacket wall is thus prevented. The gap must not be too large, so that sufficient gas pressure can accumulate in the back inner chamber in order to accelerate the plunger. The gas film also prevents overheating of the compressed gas motor during operation by reducing the friction between the plunger and the cylinder jacket wall and because the expanded gas stream of the compressed gas provides cooling.

The cross-sectional area is based on an axis perpendicular to the cylinder axis of the hollow cylinder.

Preferably, the gap is less than 50 μm wide and particularly preferably less than 10 μm wide. Moreover, the gap can be at least 0.5 μm wide and particularly preferably at least 1 μm wide.

This gap may amount to a few micrometers. Plunger rings or O-rings are not necessary for operation of the compressed gas motor. Material and assembly costs may thereby be kept low. An advantage of the gap is that, on pressurization, compressed gas flowing through the gap reduces the sliding friction between the plunger edge and the internal wall of the hollow cylinder. A further advantage is that the frictional heat is at least partially dissipated by the flowing compressed gas. The compressed gas thereby has a certain cooling function.

The position of the at least one ventilation opening in the cylinder jacket wall along the axial extent of the hollow cylinder determines the stroke of the plunger with the drive rod.

In this way, it is ensured that return of the plunger by the at least one compression spring and/or the at least one tension spring is triggered by ventilation of the back inner chamber. Due to the mass inertia of the plunger and due to the time needed for pressure compensation, overshooting beyond the at least one ventilation opening occurs.

The position of the at least one ventilation opening along the axial extent of the hollow cylinder defines the stroke of the plunger with the drive rod. This means that the closer the at least one ventilation opening is arranged towards the front base, the greater is the stroke of the plunger and of the drive rod. The closer the at least one ventilation opening is arranged towards the rear closure, the smaller is the stroke of the plunger with the drive rod. In this way, the stroke of the plunger and the drive rod and thus also the frequency of the compressed gas motor may be adapted to the respectively desired application of the compressed gas motor.

Preferably, the plunger passes fully over the at least one ventilation opening during operation of the compressed gas motor or passes fully over at least one of the at least one ventilation openings.

The objects which form the basis of the present invention are also achieved by a surgical drive system including a compressed gas motor according to the invention and a valve element, in particular a manually actuatable valve element, wherein the valve element is arranged in a compressed gas line which is connected with one of the at least one compressed gas port and which is connectable or connected with a compressed gas reservoir, such that the connection to the compressed gas reservoir is interruptible and/or the pressure at the at least one compressed gas port is adjustable with the valve element.

The surgical drive system has the advantages of the compressed gas motor according to the invention. In addition, it is comfortably usable by the actuatable valve element.

The surgical drive system has a handle, by which it is held in a hand and the valve element is actuatable with the same hand via a trigger on the handle.

In this way, handling of the surgical drive system is simplified.

Moreover, a sterile filter is arranged in the compressed gas line.

In this way, it is ensured that no contaminated or non-sterile air or non-sterile compressed gas reaches the operating room when the surgical drive system is used. The sterile filter cleans the compressed gas and thereby ensures that the compressed gas is free of microorganisms. After expansion in the compressed gas motor, the expanded gas may be output into the surrounding atmosphere without causing microbial contamination. A separate line for returning the expanded compressed gas is thus not necessary.

Preferably, the sterile filter is connected with a pressure relief valve. In this way, damage to the surgical drive system by possible overpressure of the compressed gas in the sterile filter is prevented.

The surgical drive system preferably has a housing. The handle (where present) is preferably formed by the housing. Conventional plastic half-shells produced by plastic injection molding are feasible as the housing, these being capable of being latched together or welded, riveted, screwed and/or adhesively bonded together.

The objects underlying the present invention are also achieved by a medical lavage system for debridement of soft tissue and/or bone tissue including a compressed gas motor according to the invention or a surgical drive system according to the invention.

The objects underlying the present invention are furthermore also achieved by a medical device for brushing, rasping or sawing soft tissue and/or bone tissue, including a compressed gas motor according to the invention or a surgical drive system according to the invention, wherein a tool, in particular a saw, a rasp or a brush is preferably fastened to the drive rod of the medical device.

The medical lavage system or the medical device have the advantages of the compressed gas motor according to the invention or of the surgical drive system according to the invention.

The objects underlying the present invention and relating to the method are achieved by a method for operating a compressed gas motor, in which a plunger oscillates in a linear and axial manner in a hollow cylinder, wherein the plunger is connected with a drive rod, which projects out of the hollow cylinder and drives the drive rod, wherein the method comprises the following chronological steps:

A) in an initial state, the plunger delimits a back inner chamber of the hollow cylinder, which is closed relative to the surroundings of the compressed gas motor apart from at least one compressed gas port;

B) introducing a compressed gas into the back inner chamber of the hollow cylinder through the at least one compressed gas port;

C) pushing the plunger together with the drive rod towards a front end of the hollow cylinder with enlargement of the back inner chamber using the gas pressure of the compressed gas in the back inner chamber;

D) tensioning at least one compression spring and/or at least one tension spring by movement of the plunger;

E) opening at least one ventilation opening in a cylinder jacket wall of the hollow cylinder to the back inner chamber by the movement of the plunger, wherein the at least one ventilation opening is opened directly into the back inner chamber;

F) flowing of the compressed gas out of the back inner chamber through the at least one ventilation opening, G) returning the plunger by application of the force of the at least one compression spring and/or at least one tension spring to the plunger; and H) closing the at least one ventilation opening relative to the back inner chamber through the movement of the plunger.

The method is performed with a compressed gas motor according to the invention or with a surgical drive system according to the invention or with a lavage system according to the invention or with a medical device according to the invention for brushing, rasping or sawing soft tissue and/or bone tissue.

In this way, the advantages resulting from the structural features are achieved during the course of the method.

Steps B) to H) or C) to H) can be repeated after step H), providing a compressed gas is fed into the back inner chamber via the at least one compressed gas port.

In this way, the movement of the method is periodically continued. In this way, the method may be readily used as a drive for a tool or a pump, providing compressed gas is available.

Moreover, a tool or a pump can be driven by the movement of the drive rod or of the plunger, in particular a medical tool such as a saw, a rasp or a brush or a lavage attachment.

The method for pumping, spraying, sawing, rasping or brushing may thus be used, in particular, in the medical field.

Moreover, the plunger can slide in the hollow cylinder on a gas film of the compressed gas, which flows through a gap between the plunger and the internal wall of the hollow cylinder.

In this way, the movement of the plunger is guided in a low-friction manner, such that a relatively large part of the energy applied is converted into movement and the compressed gas motor does not overheat during operation. In particular, the plunger and the cylinder jacket wall are cooled by flow through the gap of the compressed gas expanded in the back inner chamber.

Underlying the invention is the surprising recognition that such a simple construction with just one plunger, which is used simultaneously to open and close the at least one ventilation opening and as a working plunger, in a hollow cylinder enables a reliably operating compressed gas motor, which may be manufactured fully of plastic or largely of plastic, and at the same time allows a simple method for operating the motor. In this way, the compressed gas motor may be used as a relatively inexpensive single-use motor in hygienically sensitive medical fields. Durability is not necessary.

The invention is also based on the surprising recognition that with the compressed gas motor according to the invention no inlet and outlet valves or slide gates are necessary in order to drive a plunger motor by compressed air or compressed gas which generates a periodic, linearly oscillating motion. On introducing compressed gas into the back inner chamber, the plunger with the drive rod is moved by the expanding compressed gas in a fraction of a second towards the front base of the hollow cylinder, wherein at the same time the at least one compression spring is compressed and/or the at least one tension spring is extended. As a result of the inertia of the plunger and in particular of the drive rod, the plunger passes over the at least one ventilation opening and further compresses the at least one compression spring and/or extends the at least one tension spring. The at least partly expanded gas located in the back inner chamber may exit through the exposed at least one ventilation opening into the surrounding atmosphere. The pressure in the back inner chamber reduces. At the same time, the at least one compression spring and/or the at least one tension spring relaxes and respectively pushes or pulls the plunger over the at least one ventilation opening back into the starting position. The newly inflowing compressed gas causes the described process to repeat.

Measurements have shown that up to 4,000 strokes per minute are achieved with such a compressed gas motor with compressed air at a pressure of 5 bar. The compressed gas motor always started irrespective of its position. It is surprising that it is possible with the compressed gas motor made of plastic to drive saws and rasps, for the drive of which significant mechanical power is needed, using at least one sufficiently strong compression spring and/or tension spring.

An exemplary compressed gas motor according to the invention is composed of:
a) a hollow cylinder,
b) a gas-tight rear closure of the rear base of the hollow cylinder,
c) a front closure of the front base of the hollow cylinder, wherein the front closure has a central hole,
d) a plunger axially movable in the hollow cylinder, which is connected to a rod as a drive rod which projects out of the hole in the front closure,
e) a back inner chamber of the hollow cylinder delimited by the plunger, the inner wall of the hollow cylinder and the rear closure,
e) a front inner chamber of the hollow cylinder delimited by the plunger, the inner wall of the hollow cylinder and the front closure,
g) a compressed gas feed line, which is connected for passage of gas with the back inner chamber,
h) at least one ventilation opening in the jacket of the hollow cylinder, whereby the front inner chamber of the hollow cylinder is connectable for passage of gas with the surrounding atmosphere,
i) at least one spring arranged in the front inner chamber as a compression spring, wherein the spring rests against the front closure, and wherein
j) the spring pushes the plunger when not exposed to compressed gas so far towards the rear closure that the at least one ventilation opening ventilates the front inner chamber and the back inner chamber is closed relative to the surrounding atmosphere.

The hollow cylinder, the plunger, the rear closure and (where present) the front closure may be produced in a simple manner by plastic injection molding. The drive rod and the at least one compression spring and/or the at least one tension spring are preferably made of metal, particularly preferably of steel.

An exemplary medical drive device may be constructed of:
1. a flexible compressed gas feed line,
2. a sterile filter connected for passage of gas to the compressed gas feed line,
3. a valve connected to the sterile filter and designed for manual actuation,
4. a compressed gas line connected for passage of gas to the valve,
5. a compressed gas motor, which is connected for passage of gas to the compressed gas line, wherein the compressed gas motor is composed of
a) a hollow cylinder,
b) a gas-tight rear closure of the rear base of the hollow cylinder,
c) a front closure of the front base of the hollow cylinder, wherein the front closure has a central hole,
d) a plunger axially movable in the hollow cylinder, which is connected to a rod as a drive rod which projects out of the hole in the front closure,
e) a back inner chamber of the hollow cylinder delimited by the plunger, the inner wall of the hollow cylinder and the rear closure,
e) a front inner chamber of the hollow cylinder delimited by the plunger, the inner wall of the hollow cylinder and the front closure,
g) a compressed gas feed line, which is connected for passage of gas with the back inner chamber,
h) at least one ventilation opening in the jacket of the hollow cylinder, whereby the front inner chamber of the hollow cylinder is connectable for passage of gas with the surrounding atmosphere,
i) at least one spring arranged in the front inner chamber as a compression spring, wherein the spring rests against the front closure, and wherein
j) the spring pushes the plunger when not exposed to compressed gas so far towards the rear closure that the at least one ventilation opening ventilates the front inner chamber and the back inner chamber is closed relative to the surrounding atmosphere,
6. a tool, which is connected with the rod of the compressed gas motor, and
7. a housing, which at least in part encloses the compressed gas motor, the compressed gas line, the sterile filter and the valve, wherein the inner chamber of the housing is connected for passage of gas with the surrounding atmosphere.

The compressed gas motor according to the invention may be used as a drive for lavage systems and devices for the debridement of soft tissue and bone tissue. The compressed gas motor may preferably also be used as a drive for devices for brushing, rasping and sawing soft tissue and bone tissue. Furthermore, the compressed gas motor may be used to drive medical devices for single use.

It is to be understood that both the foregoing general description and the following detailed description are exemplary, but are not restrictive, of the disclosure.

DESCRIPTION OF THE DRAWING

The disclosure is best understood from the following detailed description when read in connection with the accompanying drawing. Further exemplary embodiments of the invention are explained below with reference to sixteen schematically depicted figures without thereby limiting the invention in any way. Included in the drawing are the following figures.

DETAILED DESCRIPTION OF THE DISCLOSURE

The invention relates to a compressed gas motor, a surgical drive system with such a compressed gas motor, a medical lavage system for debridement of soft tissue and/or bone tissue including such a compressed gas motor and a medical device for brushing, rasping or sawing of soft tissue and/or bone tissue with such a compressed gas motor as well as to a method for operating a compressed gas motor. The compressed gas motor is suitable for driving medical devices for lavage and debridement of soft and bone tissue. For reasons of hygiene, the medical devices driven by the compressed gas motor are preferably intended for single use.

The subject of the present invention is in particular a simplified compressed gas motor and a surgical, i.e., a medical drive system with the simplified compressed gas motor. The simplified compressed gas motor and the surgical drive system consist substantially of plastic and are intended and suitable for single use.

In the figures and the following description of the exemplary embodiments of the present invention explained with reference to the figures, some of the same reference signs are used for the same or similar parts in different exemplary embodiments and for different individual parts in order to simplify comparability of the exemplary embodiments and readability.

Figure 1:
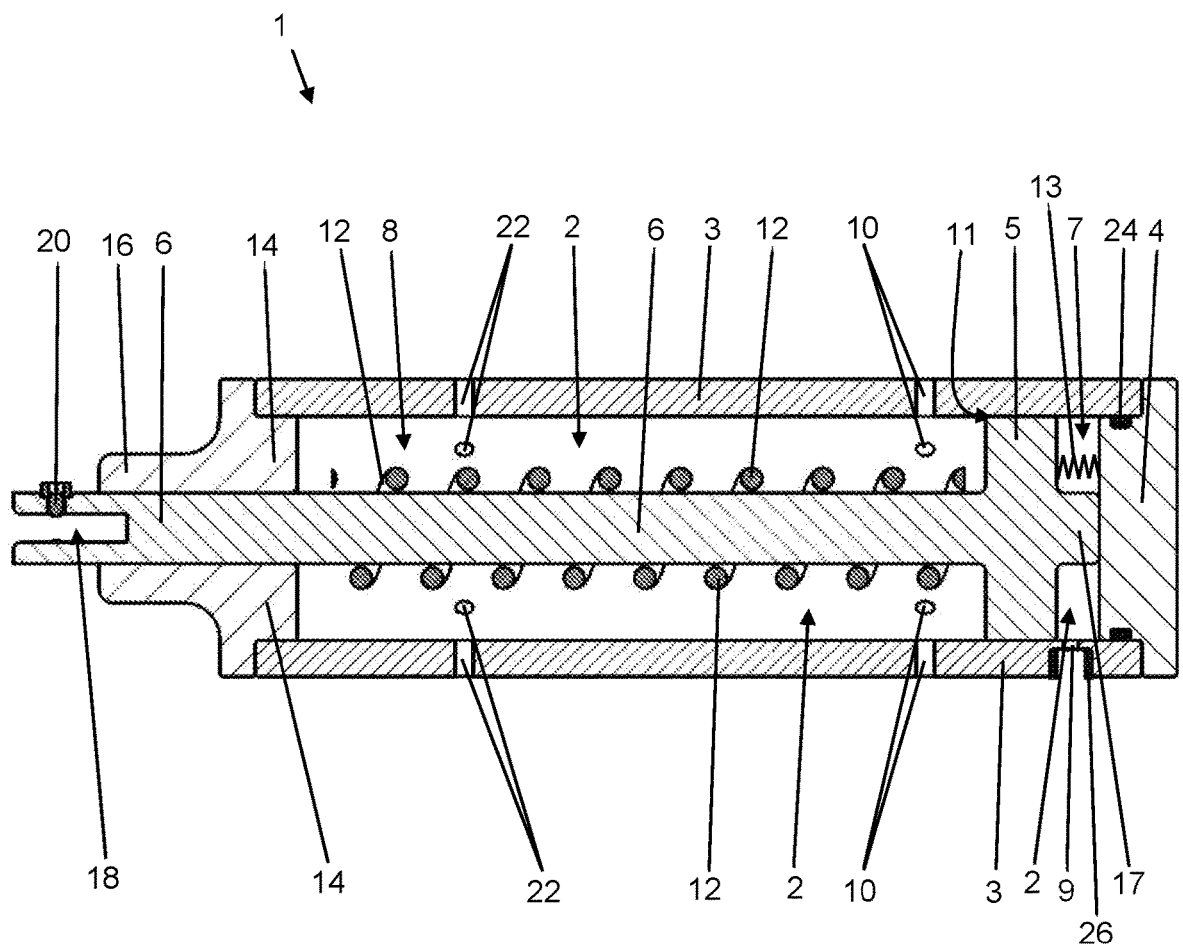
FIG. 1 is a schematic cross-sectional view of an exemplary compressed gas motor according to the invention in the idle state.
Figure 2:
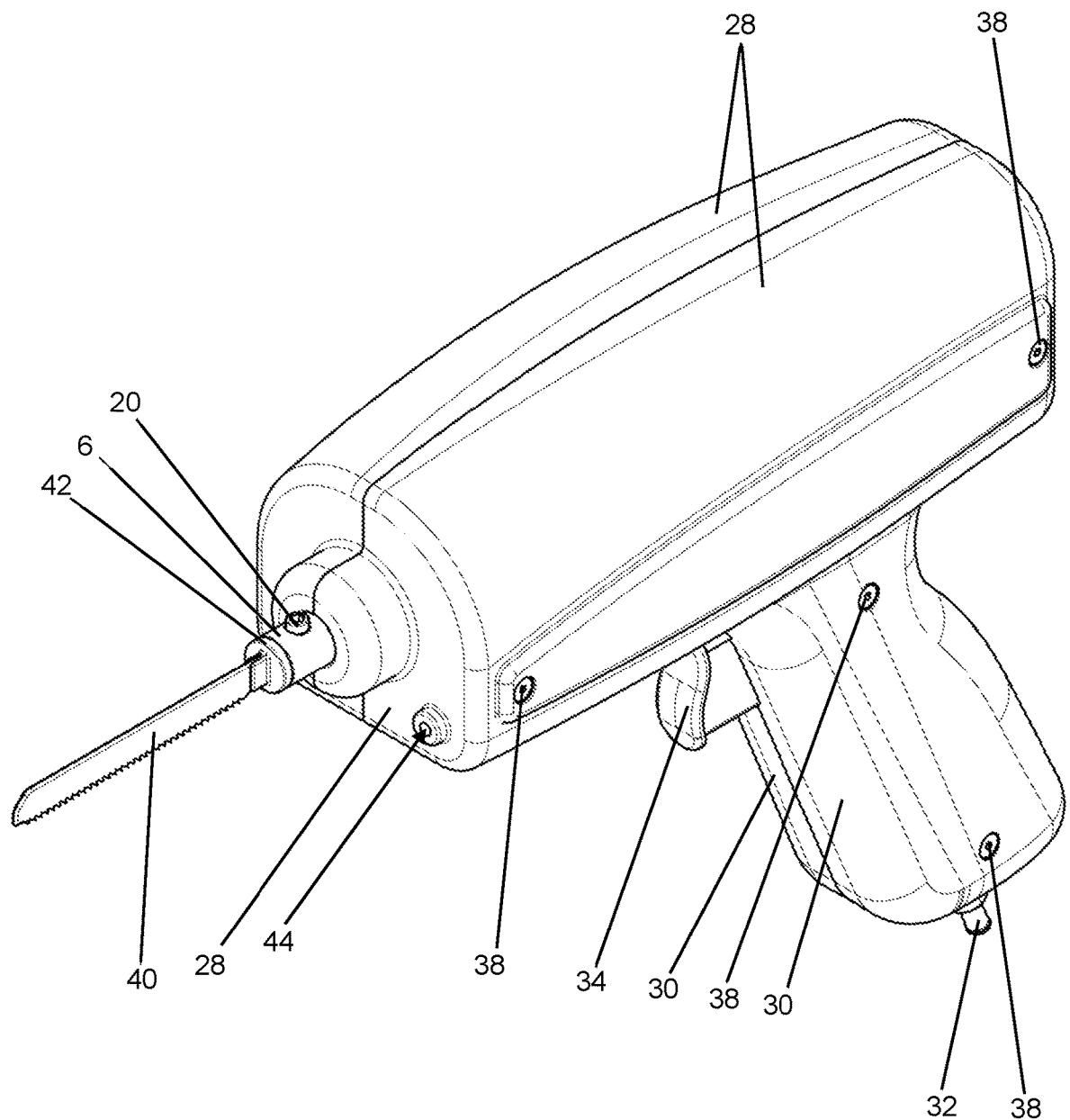
FIG. 2 is a schematic perspective view of a surgical drive system according to the invention containing a compressed gas motor according to the invention, wherein a bone saw is fastened to the drive system.
Figure 3:
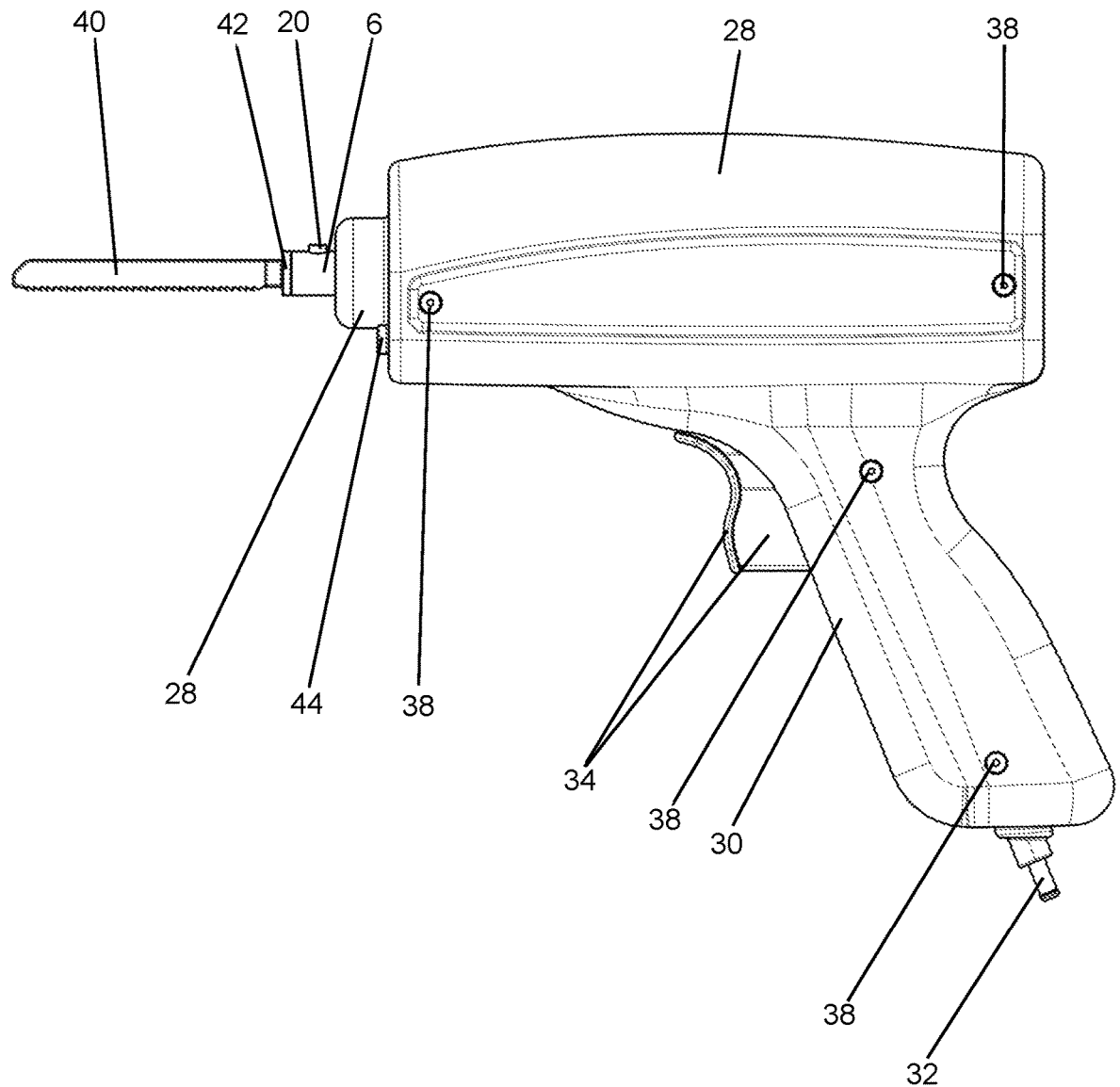
FIG. 3 is a schematic side view of the surgical drive system according to FIG. 2.

FIG. 1 shows a schematic cross-sectional view of an exemplary compressed gas motor 1 according to the invention in the idle state. FIGS. 2 to 5 show various perspective views of an exemplary surgical drive system according to the invention with the compressed gas motor 1 according to the invention. FIGS. 6 to 11 are cross-sectional views of an exemplary surgical drive system according to the invention with the compressed gas motor 1 according to the invention, with which the course of a method according to the invention is conducted. FIGS. 12 to 16 show a surgical drive system according to the invention with the compressed gas motor 1 according to the invention and different attachments, which can be used in surgery and can be driven with the surgical drive system. The exemplary compressed gas motor 1 according to the invention shown in FIG. 1 could easily also be used, however, to drive other tools or other actuators for non-medical purposes.

Figure 4:
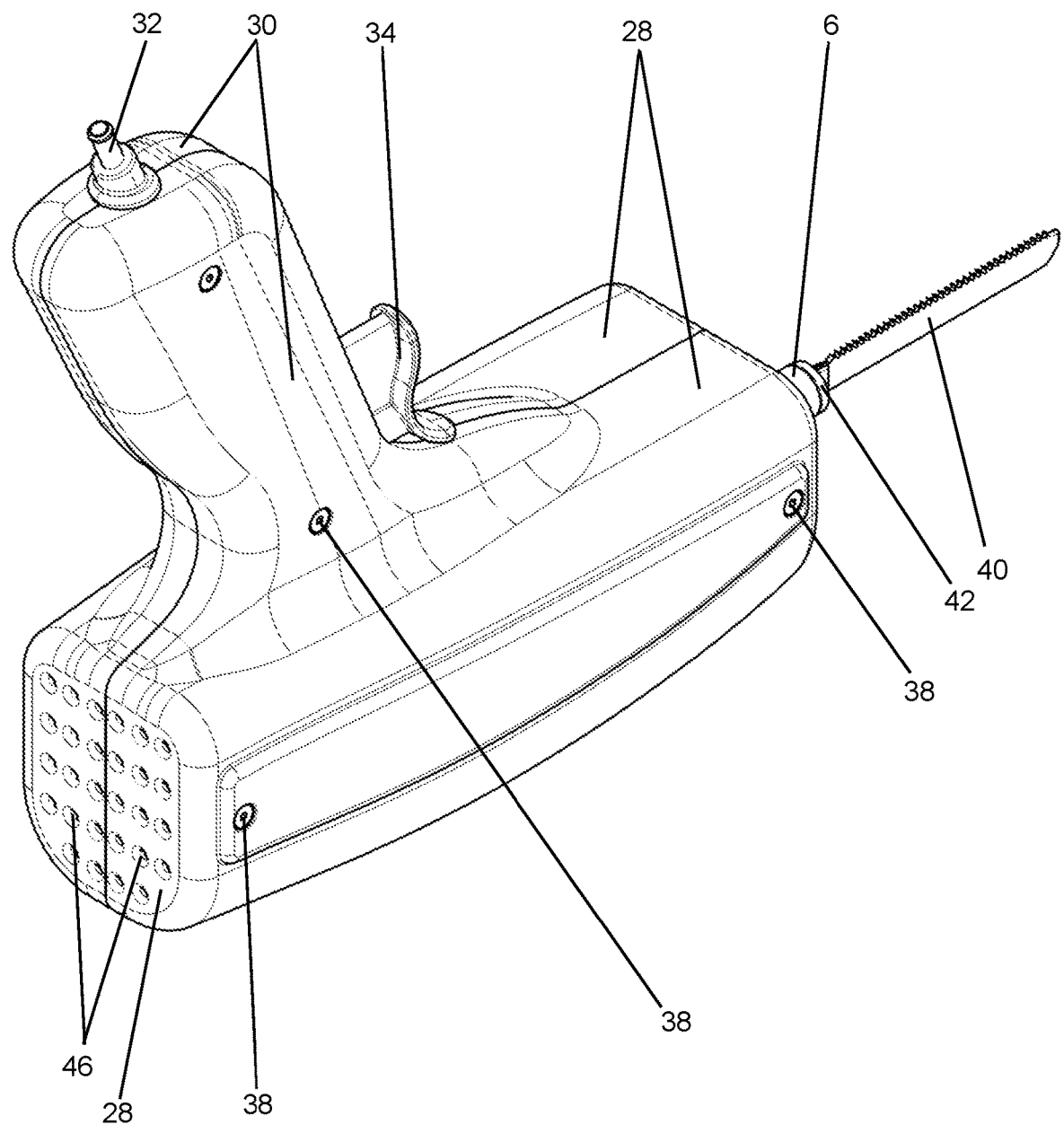
FIG. 4 is a schematic perspective view of the bottom and back of the surgical drive system according to FIGS. 2 and 3.
Figure 5:
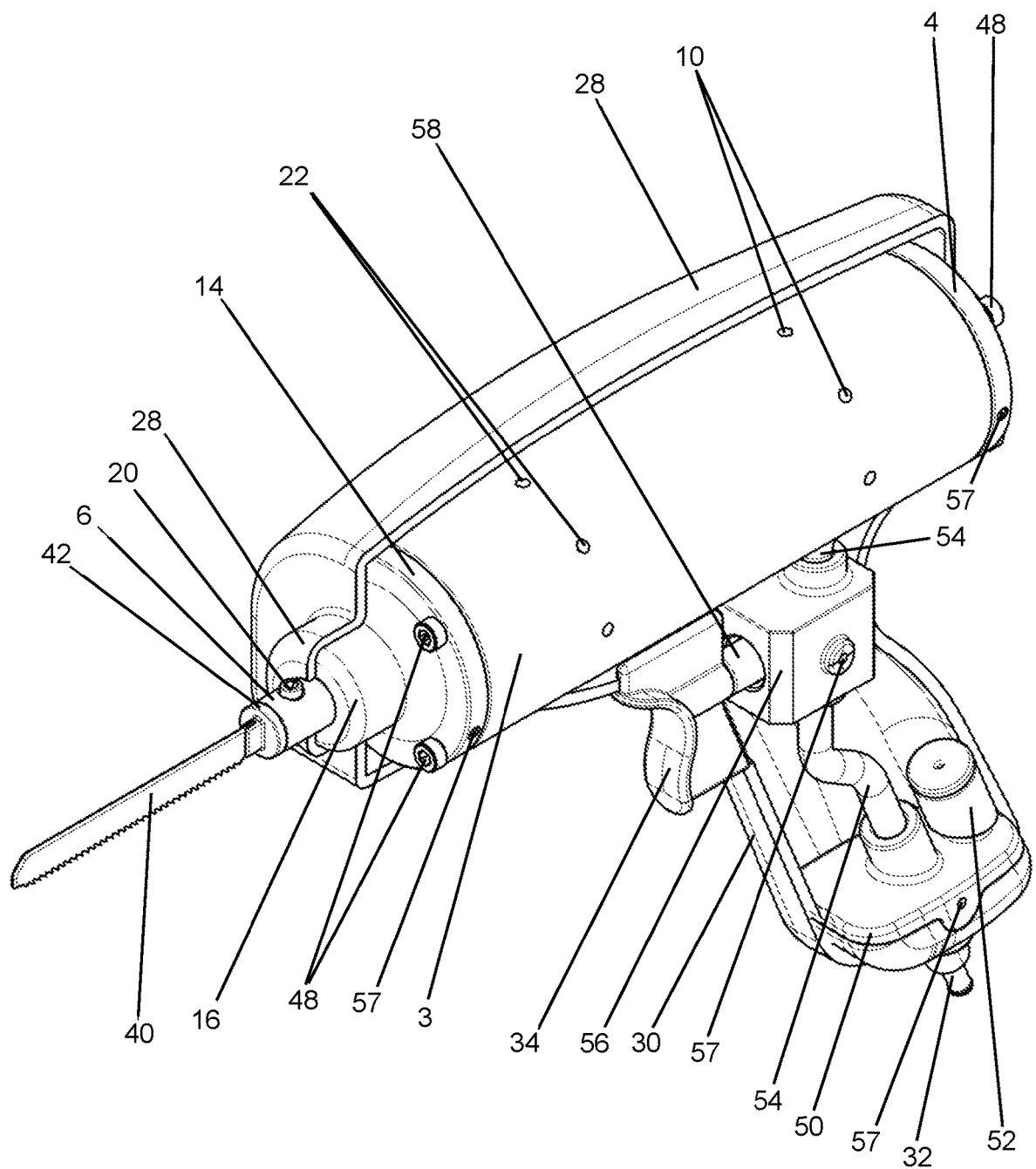
FIG. 5 is a schematic perspective view of the top and front of the surgical drive system according to FIGS. 2 and 4, with the housing open.
Figure 6:
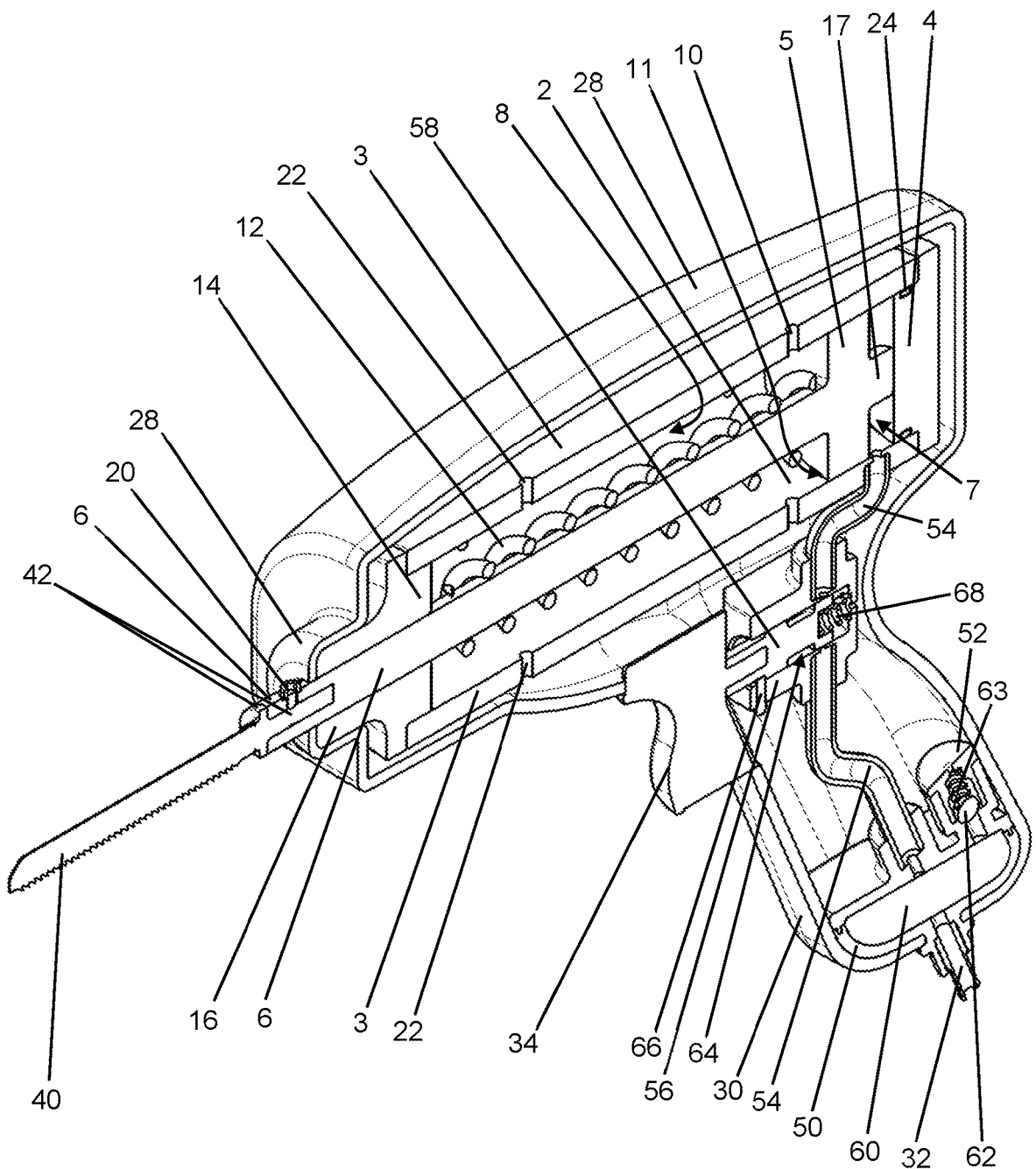
FIG. 6 is a schematic perspective cross-sectional view of the surgical drive system according to FIGS. 2 to 5 with the compressed gas motor in the initial state.
Figure 7:
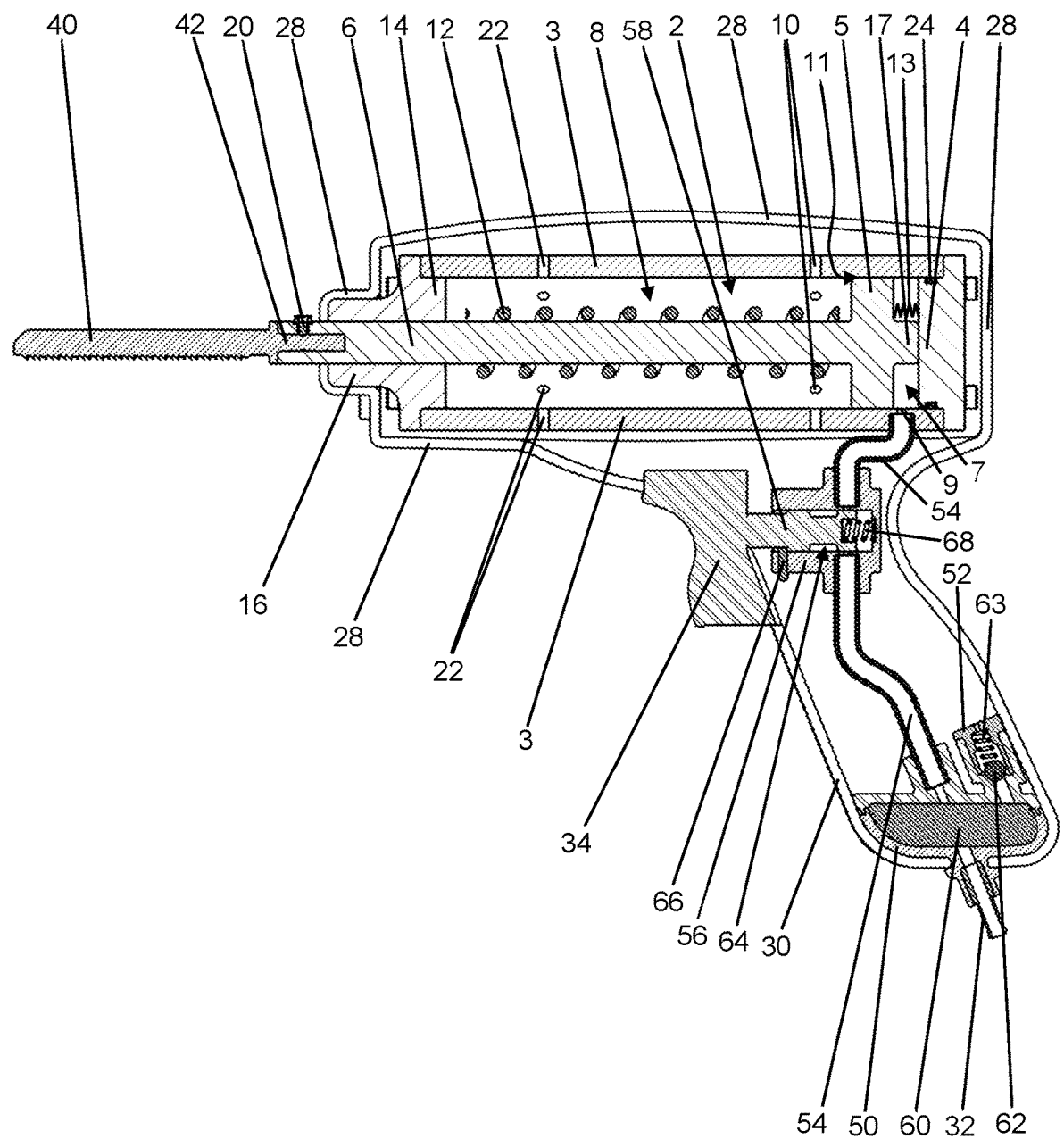
FIG. 7 is a schematic cross-sectional view of the surgical drive system according to FIGS. 2 to 6 with the compressed gas motor in the initial state.

The front ends of the compressed gas motors and the surgical drive systems point to the left in FIGS. 1 to 3 and 5 to 16 and backwards and to the right in FIG. 4. Accordingly, the rear ends of the compressed gas motors and the surgical drive systems point to the right in FIGS. 1 to 3 and 5 to 16 and forwards and to the left in FIG. 4.

The first exemplary compressed gas motor 1 according to the invention includes a hollow cylinder 2 of plastic delimited by a tubular cylinder jacket wall 3 of plastic. At its rear end (on the right in FIG. 1), the hollow cylinder 2 is closed with a rear closure 4 of plastic. The rear closure 4 then defines with its front surface a rear base of the hollow cylinder 2. Inside the hollow cylinder 2 a plunger 5 of plastic is arranged in an axially movable manner. The term "axial" relates to the cylinder axis of the hollow cylinder 2. At the front end of the plunger 5 (on the left in FIG. 1) a drive rod 6 of metal or plastic is arranged which may be fixed to the plunger 5 or integral with the plunger 5. By "integral" is meant a single piece or a single unitary part that is complete by itself without additional pieces, i.e., the part is of one monolithic piece formed as a unit with another part. The plunger 5 subdivides the hollow cylinder 2 into a back inner chamber 7 and a front inner chamber 8. The back inner chamber 7 is supplied via a compressed gas port 9 in the cylinder jacket wall 3 with a compressed gas 70 (see FIGS. 8 to 11), such as for example compressed air or $CO_2$ gas from a $CO_2$ cartridge.

The plunger 5 has a cylindrical outer circumference which is somewhat smaller than the internal diameter of the hollow cylinder 2. In this way, a small gap 11 is provided between the plunger 5 and the hollow cylinder 2. Through this gap 11 a compressed gas can flow from the back inner chamber 7 into the front inner chamber 8 at a low volumetric flow rate. In this way, the plunger 5 can slide in the hollow cylinder 2 on an air film or compressed gas film and consequently has less of a tendency to jam. The gap 11 must be kept small enough for the volumetric flow rate through the gap 11 to be smaller than the volumetric flow rate through the compressed gas port 9, so that sufficient overpressure builds up or accumulates in the back inner chamber 7 to drive the plunger 5. To this end, the cross-section of the gap 11 is preferably less at least by a factor of ten than the cross-section of the compressed air port 9.

Figure 11:
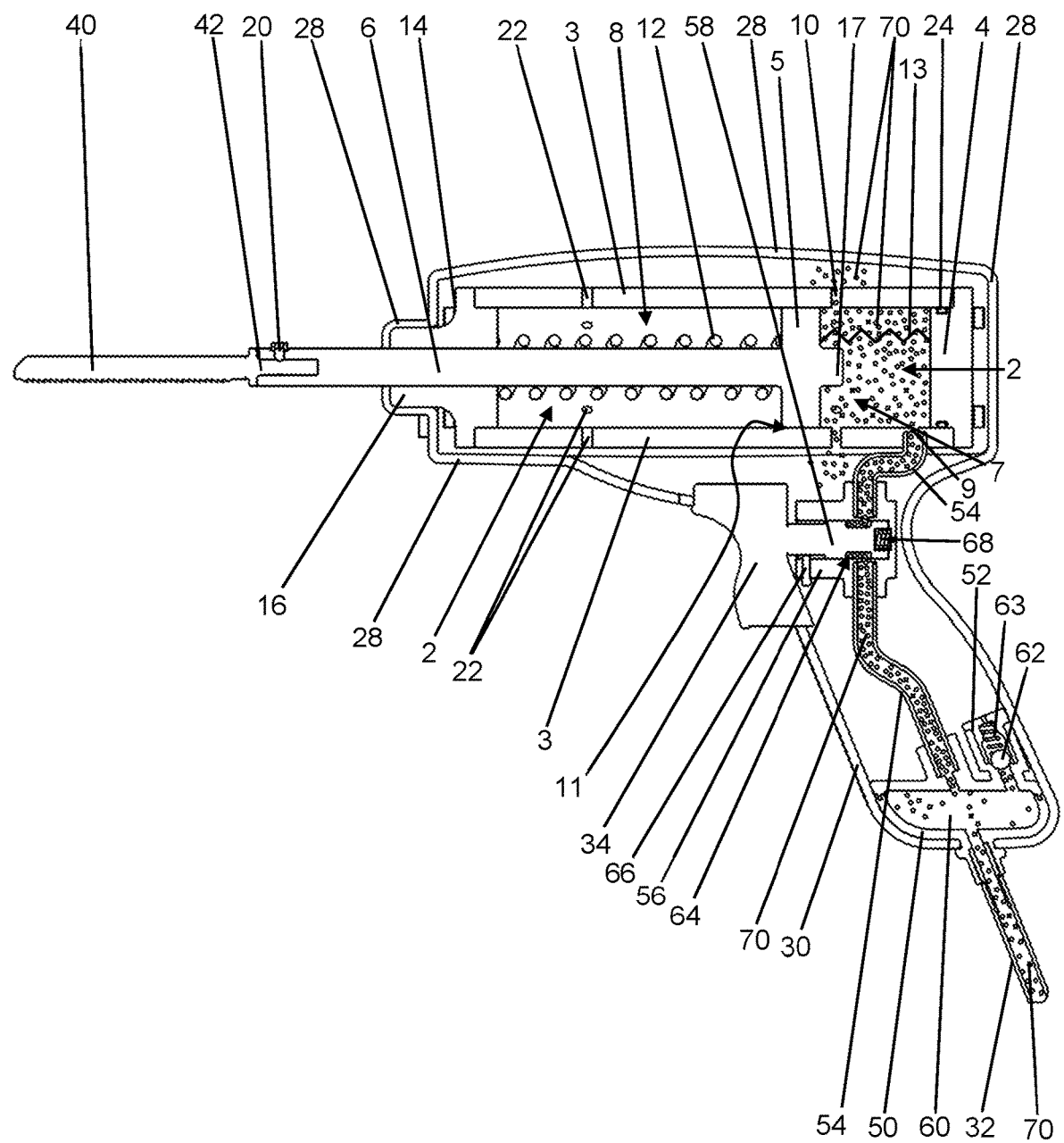
FIG. 11 is a schematic cross-sectional view of the surgical drive system according to FIGS. 2 to 10 with the compressed gas motor in operation during discharge of compressed gas from the compressed gas motor.

In a back region of the cylinder jacket wall 3 eight ventilation openings 10 are arranged, through which the compressed gas 70 can escape from the back inner chamber 7 when the plunger 5 has been deflected forwards (see FIG. 11). A compression spring 12 is arranged in the front inner chamber 8 around the drive rod 6. The compression spring 12 is tensioned when the plunger 5 is urged by the compressed gas 70 towards the front end. In the process, the compression spring 12 rests on a front closure 14 of plastic. The front closure 14 closes the hollow cylinder 2 at the front end thereof (on the left in FIG. 1) and thereby defines with its rear surface a front base of the hollow cylinder 2.

A feedthrough may be arranged in the front closure 14 in which the drive rod 6 is mounted in an axially movable manner and through which the drive rod 6 extends out of the hollow cylinder 2. For more stable guidance of the drive rod 6 a guide neck 16 is arranged on the front closure 14 which lengthens the feedthrough in the front closure 14. At least one opening (not shown) allowing passage of gas may additionally be arranged in the front closure 14, by which opening the front inner chamber 8 is connected for passage of gas with the surrounding environment.

The back inner chamber 7 is delimited by the plunger 5, the cylinder jacket wall 3 and the rear closure 4. The front inner chamber 8 is delimited by the plunger 5, the cylinder jacket wall 3 and the front closure 14.

A spacer 17 is arranged on the back end of the plunger 5. The spacer 17 ensures that the plunger 5 never closes the compressed gas port 9 and thus the back inner chamber 7 is always open towards the compressed gas port 9. The spacer 17 may be embodied as an extension of the drive rod 6 through the plunger 5 or integral with both.

At the front end of the drive rod 6, which projects out of the hollow cylinder 2, a fastening element 18 is arranged in the form of a rectangular recess and a screw 20. Alternatively, the fastening element 18 may also have an internal thread. The fastening element 18 allows a tool to be connected with the drive rod 6 and driven.

In the front region of the hollow cylinder 2, over which the plunger 5 never passes, eight openings 22 allowing passage of gas are arranged in the cylinder jacket wall 3. These openings 22 allowing passage of gas enable the front inner chamber 8 to remain connected with the surroundings of the compressed gas motor 1. In this way, no problematic gas pressure can accumulate in the front inner chamber 8 which would counteract movement of the plunger 5 towards the front closure 14. Alternatively or in addition, openings (not shown) allowing passage of gas may also be arranged in the front closure 14. It is also possible not to provide any openings 22 which allow passage of gas. The gas pressure forming in the front inner chamber 8 may then be used as a compression spring element or as an additional compression spring element for returning the plunger 5 towards the rear closure 4.

In order to seal the back inner chamber 7, the rear closure 4 is sealed with a peripheral seal 24 of rubber relative to its seating in the cylinder jacket wall 3. The peripheral seal 24 is preferably an O-ring. A connection 26 for pressure-tight connection and for fastening a compressed gas line 54 (see FIGS. 5 to 11 and 13) is arranged at the compressed gas port 9.

Figure 12:
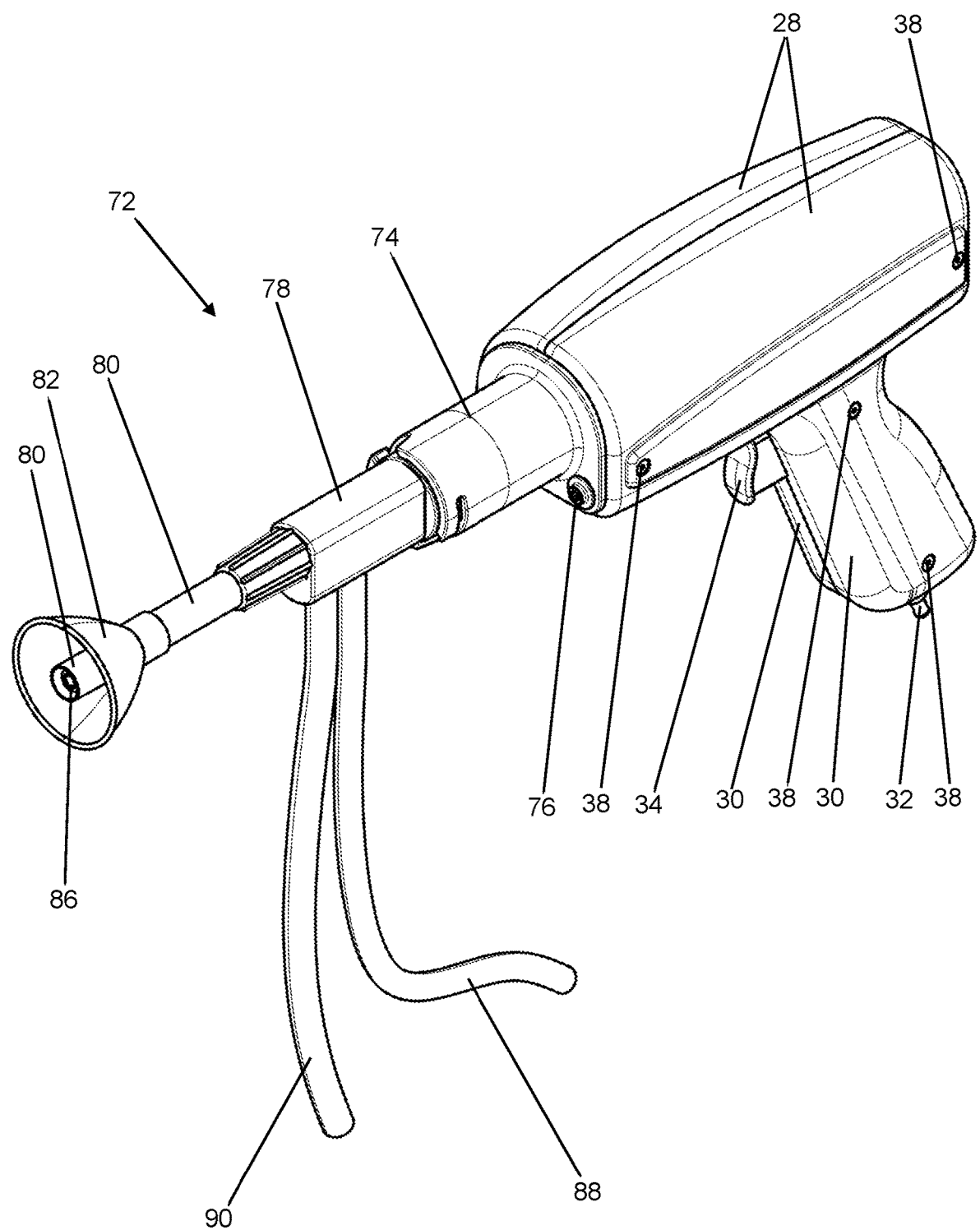
FIG. 12 is a schematic perspective view of a surgical drive system according to the invention containing a compressed gas motor according to the invention, wherein a lavage attachment is fastened to the drive system.
Figure 13:
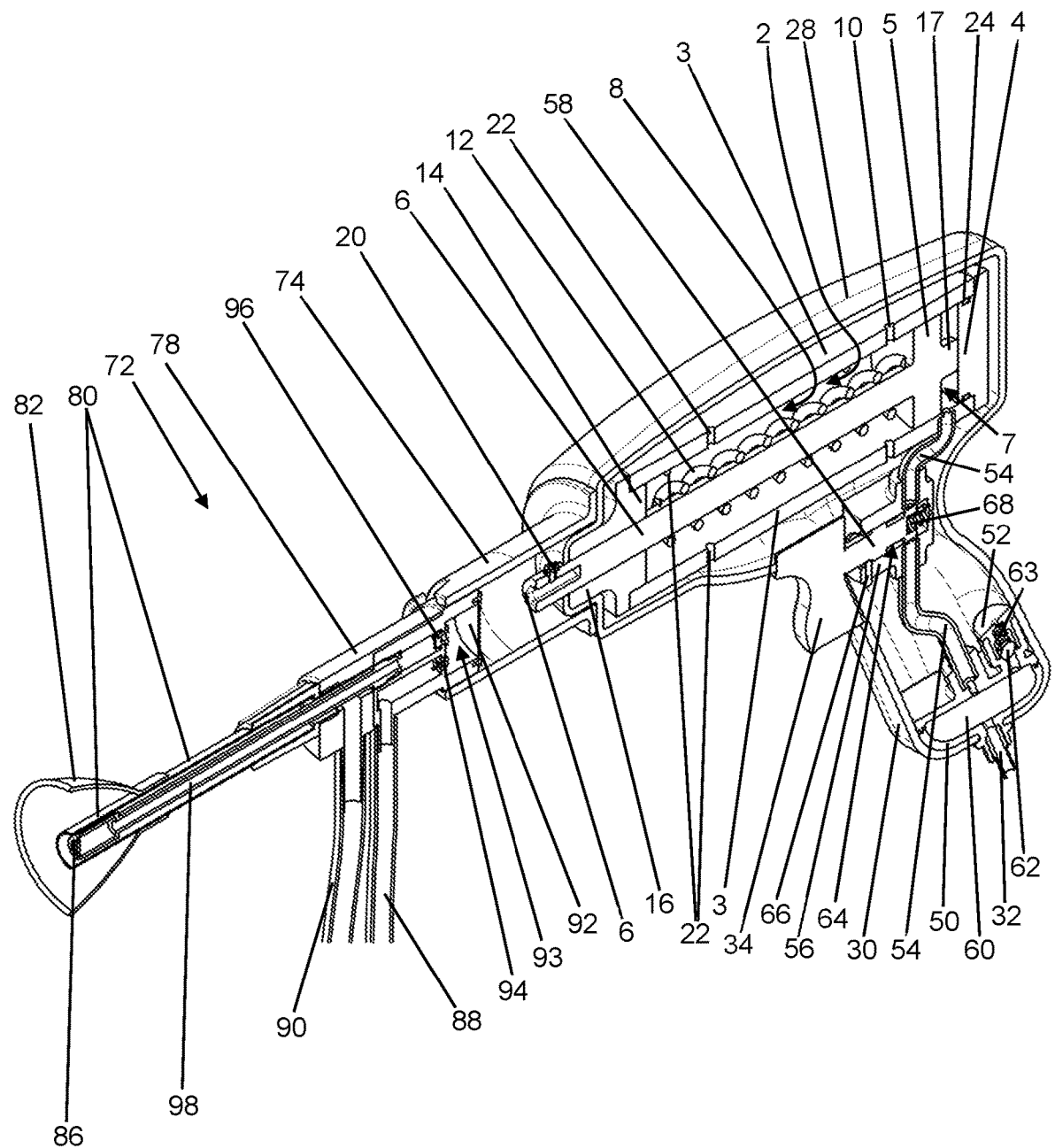
FIG. 13 is a schematic perspective cross-sectional view of the surgical drive system with the lavage attachment according to FIG. 12.
Figure 14:
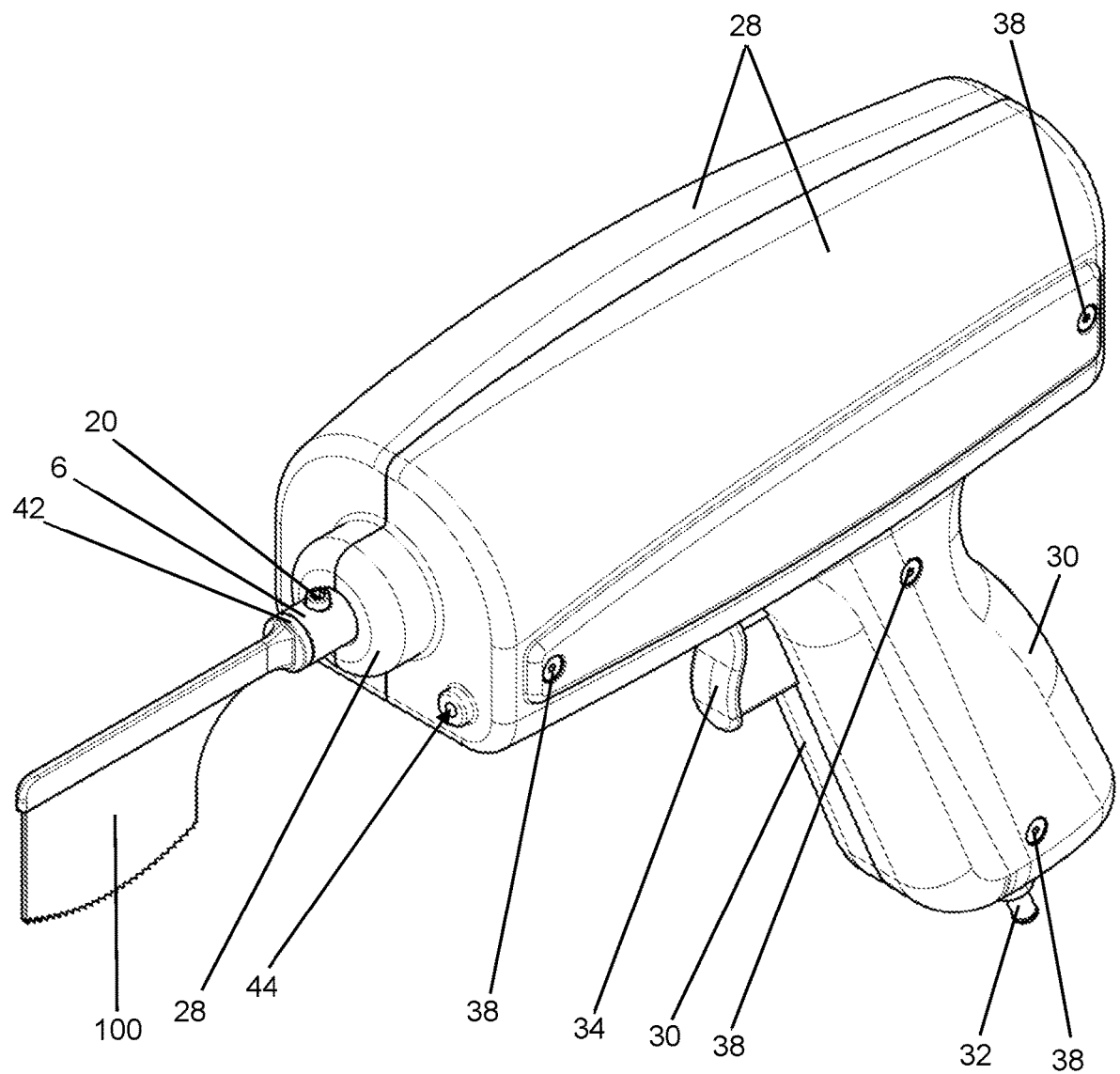
FIG. 14 is a schematic perspective view of a surgical drive system according to the invention containing a compressed gas motor according to the invention, wherein a saw is fastened to the drive system.
Figure 15:
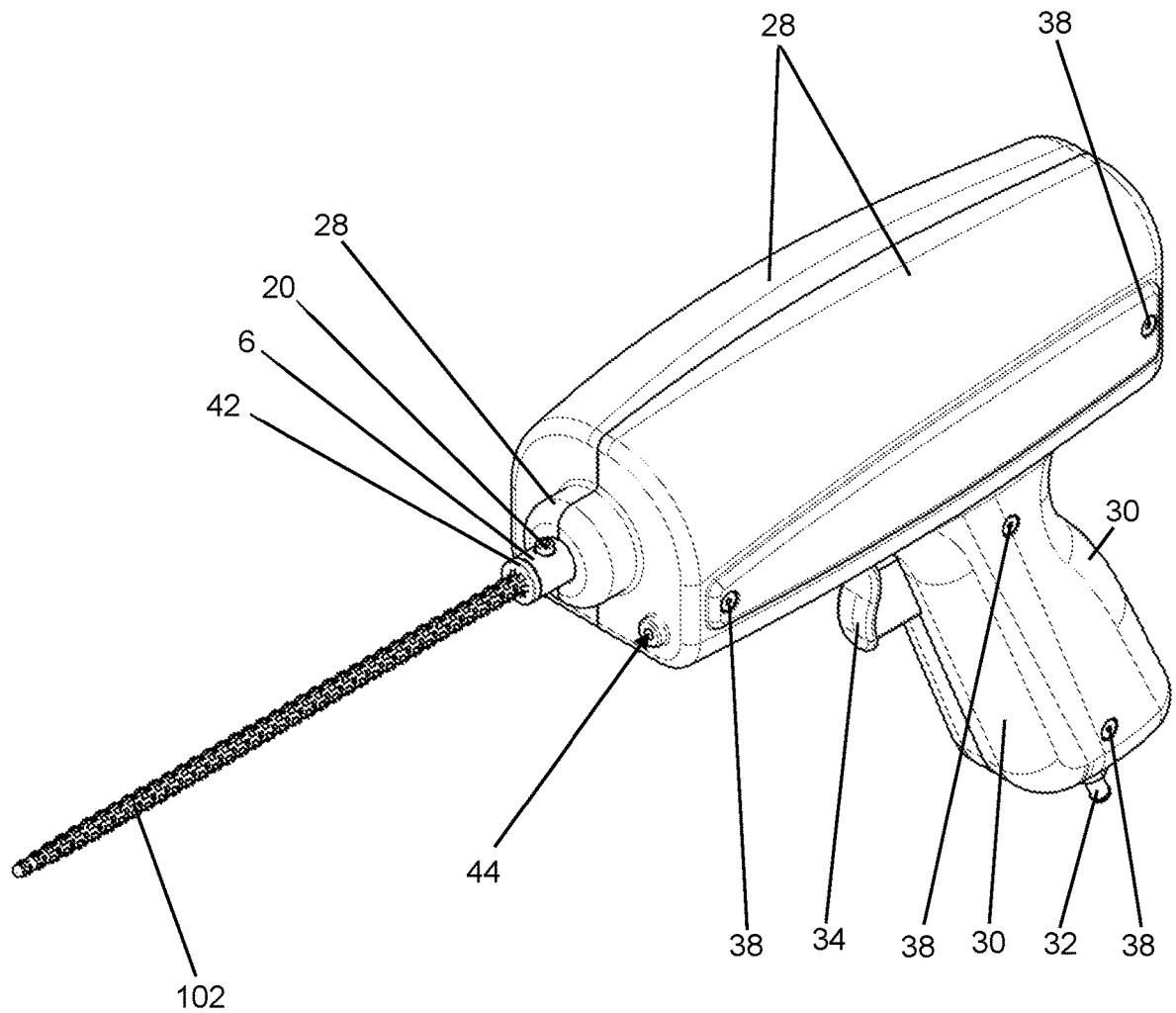
FIG. 15 is a schematic perspective view of a surgical drive system according to the invention containing a compressed gas motor according to the invention, wherein a rasp is fastened to the drive system.
Figure 16:
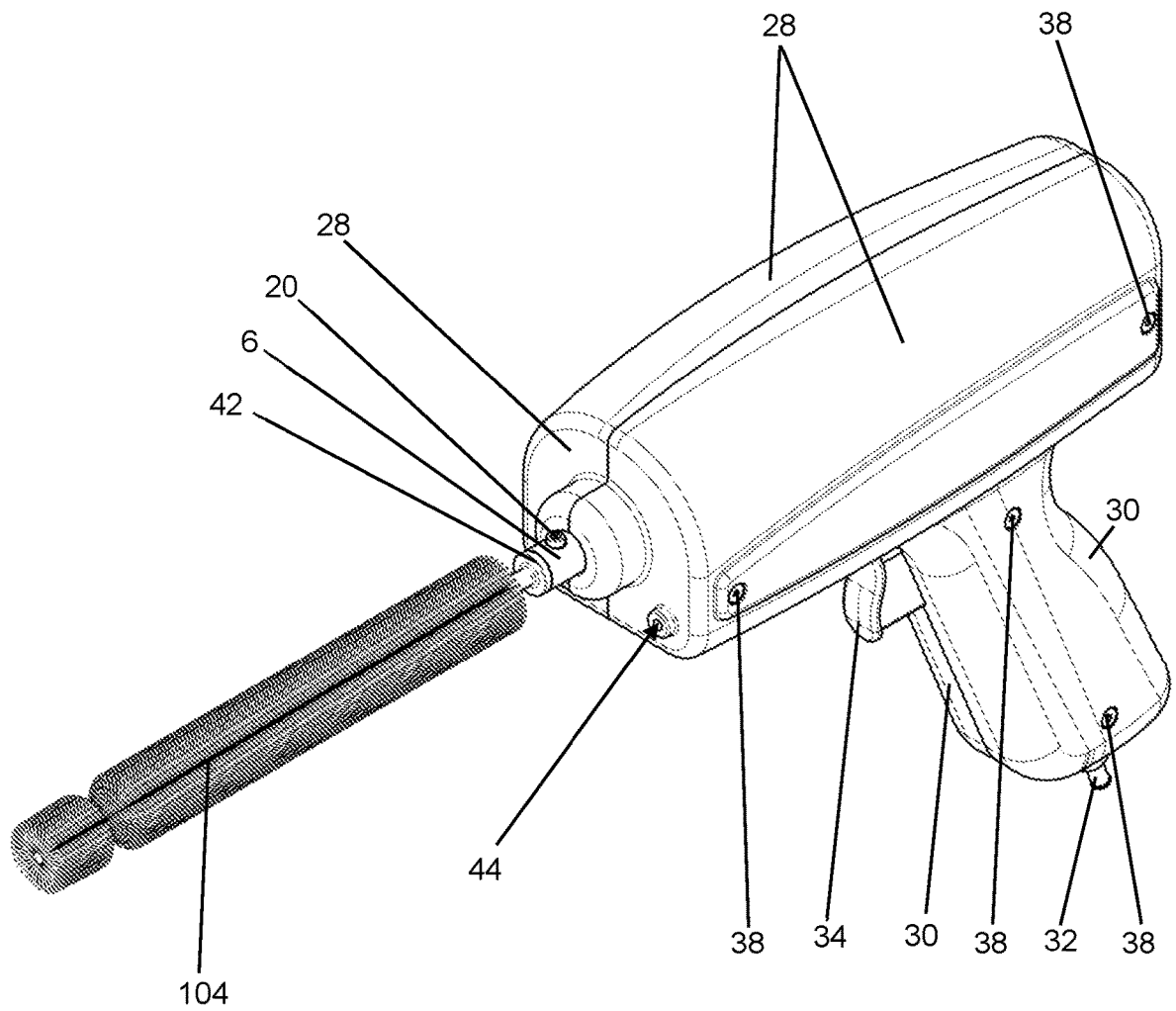
FIG. 16 is a schematic perspective view of a surgical drive system according to the invention containing a compressed gas motor according to the invention, wherein a brush is fastened to the drive system.

FIGS. 2 to 16 are schematic representations of a surgical drive system including the compressed gas motor 1 according to FIG. 1, wherein in FIGS. 2 to 11 a saw 40, in FIGS. 12 and 13 a lavage attachment 72 and in FIGS. 14 to 16 different tools are fastened to the drive system.

The surgical drive system has a two-part housing 28 of plastic or plastic material, which houses the compressed gas motor 1. The housing 28 may to this end have two substantially uniform half-shells. One part of the housing 28 takes the form of a handle 30, to make it possible to hold the surgical drive system with one hand. A compressed gas hose 32 exits the handle through which a compressed gas may be passed into the surgical drive system and therein to the compressed gas motor 1. The compressed gas hose 32 may for example have been or be connected with a compressed air reservoir or a pump for generating compressed air. Alternatively, a cartridge (not shown) with a compressed gas contained therein, such as for example a $CO_2$ cartridge, may be or have been connected. Such a compressed gas cartridge may also be arranged in the housing 28, without guiding the compressed gas hose 32 out of the housing 28.

The surgical drive system is operated by way of a trigger 34, which is arranged in the region of the handle 30. The parts of the housing 28 may be connected together with rivets or screws 38. The saw 40 may have a counter-fastening element 42 with a rectangular extension or an external thread, which fits with the fastening element 18, such that the saw 40 can be fastened detachably with the counter-fastening element 42 in the fastening element 18. To secure the saw 40, the screw 20 is tightened. A counter-fastening mechanism 44 in the form of a bore with an internal thread is arranged at the front of the housing 28, with which mechanism more complex tools such as the lavage attachment 72 may be fastened to the surgical drive system. At the rear of the housing 28 a plurality of vent openings 46 are arranged through which gas escaping from the compressed gas motor 1 inside the housing 28 may exit. The rear of the housing 28 is preferred for this, so as not to generate any air stream or gas stream at the front end in the region of the tool.

The rear closure 4 and the front closure 14 may be fastened with screws 48 to the cylinder jacket wall 3, in order to absorb the force of the gas pressure in the back inner chamber 7 and also in the front inner chamber 8. A sterile filter 60 is arranged in a sterile filter housing 50 at the bottom of the handle 30. The compressed gas hose 32 leads into the sterile filter 60. The sterile filter 60 removes microorganisms from the introduced compressed gas 70 before they can enter the compressed gas motor 1 and then be output to the surroundings. In this way, the operating room or the surroundings of the surgical drive system can be kept hygienic.

A pressure relief valve 52 is arranged on the sterile filter housing 50, with which an overpressure in the sterile filter housing 50 can be released. This makes it possible to prevent the sterile filter housing 50 from bursting. Furthermore, a compressed gas line 54 is connected to the sterile filter housing 50. The compressed gas 70 which is forced through the compressed gas hose 32 into the sterile filter 60 is then forced out of the sterile filter 60 into the compressed gas line 54 within the housing 28.

A manually operable valve element with a valve housing 56 is arranged in the compressed gas line 54. The manually operable valve element is operable with the trigger 34. Bores 57 are arranged at the valve housing 56, the front closure 14, the rear closure 4 and the sterile filter housing 50, with which bores 57 the rivets or screws 38 may be connected in order to fasten the housing 28 to the interior structure. If screws 38 are used, the bores 57 have an internal thread which fits with the screws 38. If rivets 38 are used, simple blind holes may be used as the bores 57, in which the rivets 38 are fastened as blind rivets. Alternatively or in addition, it is also possible to rivet, screw, weld and/or adhesively bond the two halves or parts of the housing 28 directly together.

The manually operable valve element has a valve 58 in the form of a cylindrical pin with a peripheral valve groove 64. The valve 58 is mounted in the valve housing 56 so as to be movable in the axial direction of the cylindrical pin, the valve housing serving as a valve seat. The valve 58 may be secured in the valve housing 56 by a bolt 66. To this end, the valve 58 has an indentation at its front end which the bolt 66 engages. The valve 58 is mounted in the valve housing 56 with a spring 68, with which the valve 58 is transferred into the closed state. At the same time, the trigger 34 is thereby urged forwards. In the closed state the valve 58 closes the compressed gas line 54 (see FIGS. 6 to 8). In the process, the valve 58, with its external circumference, fully closes the compressed gas line 54 in the valve element. To open the valve element, the valve 58 is urged with the trigger 34 against the spring 68 into the valve seat of the valve housing 56. In the process, the peripheral valve groove 64 moves into the compressed gas line 54 and thereby provides a connection allowing passage of gas.

The pressure relief valve 52 is constructed with a ball 62 and a spring 63, which urges the ball 62 into a ball seat of the pressure relief valve 52. Alternatively, a bursting disk (not shown) may also be used as the pressure relief valve 52.

In the back inner chamber 7 a tension spring 13 may be arranged, which is connected with the rear of the plunger 5 and the rear closure 4. The tension spring 13 extends on movement of the plunger 5 towards the front closure 14 and in the process is tensioned, as the compression spring 12 is compressed. The energy stored in the tension spring 13 may accordingly analogously be used to return the plunger 5 towards the rear closure 4. The tension spring 13 may be arranged in the back inner chamber 7 in addition or as an alternative to the compression spring 12 in the front inner chamber 8.

Operation of the compressed gas motor 1 or of the surgical drive system and thus an exemplary method according to the invention is explained hereinafter with reference to FIGS. 8 to 11.

Figure 8:
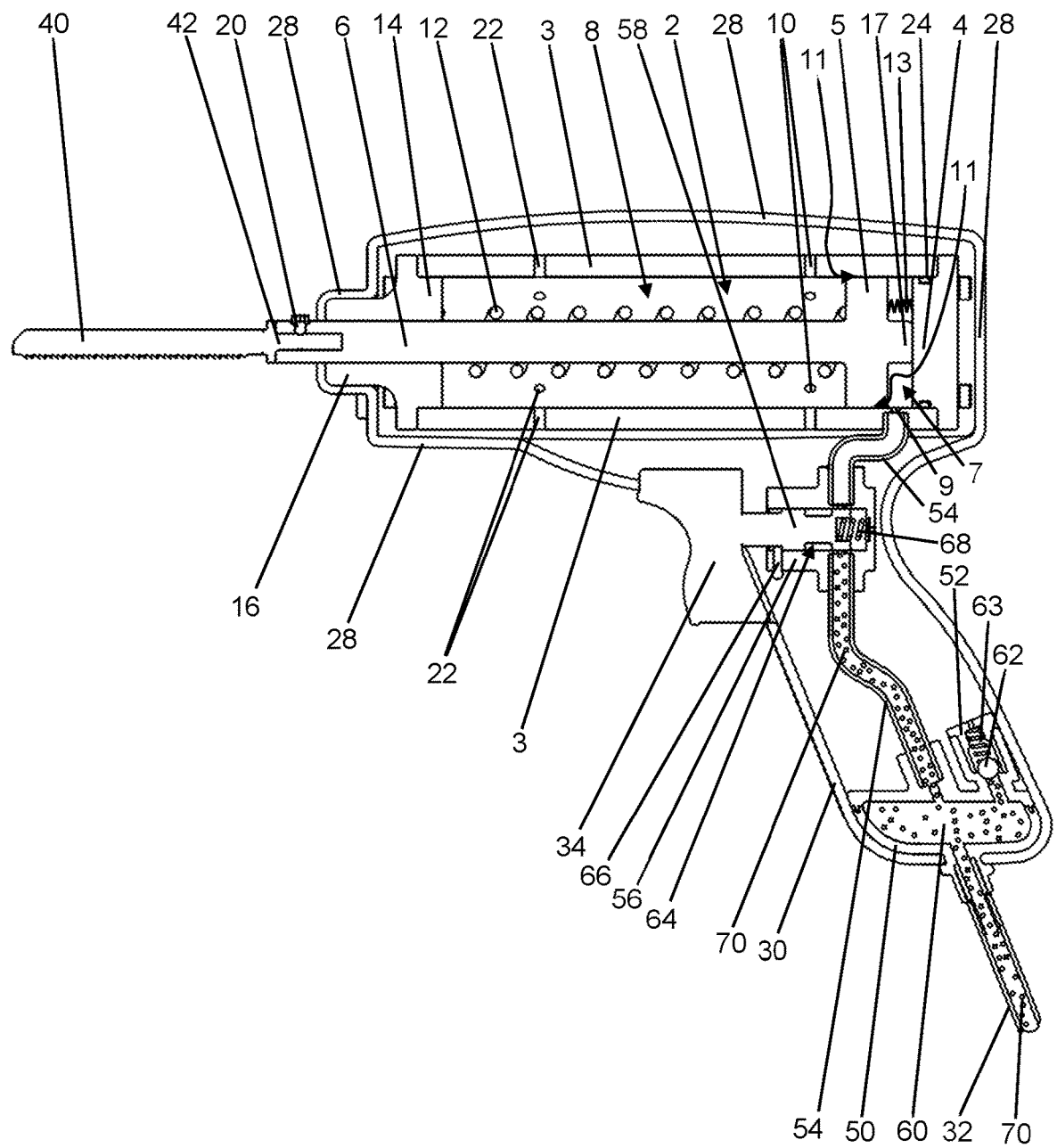
FIG. 8 is a schematic cross-sectional view of the surgical drive system according to FIGS. 2 to 7 with the compressed gas motor in the initial state with applied compressed gas.

The compressed gas 70 is passed via the compressed gas hose 32 through the sterile filter 60 to the valve element. The valve 58 initially blocks further conduction of the compressed gas 70 through the compressed gas line 54. The plunger 5 is located in a starting position, in which the compression spring 12 is urging or has urged the plunger 5 towards the rear closure 4. The plunger 5 is arranged between the ventilation openings 10 and the rear closure 4, such that the back inner chamber 7 does not lead into the ventilation openings 10. At the same time, however, the spacer 17 ensures that the compressed gas port 9 in the back inner chamber 7 is open. This situation is shown in FIG. 8. Under normal circumstances, however, the pressure of the compressed gas 70 is insufficient to open the pressure relief valve 52, i.e., to urge the ball 62 against the spring 63 out of the valve seat or to break the bursting disk.

To operate the surgical drive system, the valve 58 is urged with the trigger 34 into the valve housing 56 and thereby provides with the valve groove 64 a connection allowing passage of gas in the compressed gas line 54. During operation of the compressed gas motor 1, the trigger 34 remains pressed and thus the valve element remains open.

Figure 9:
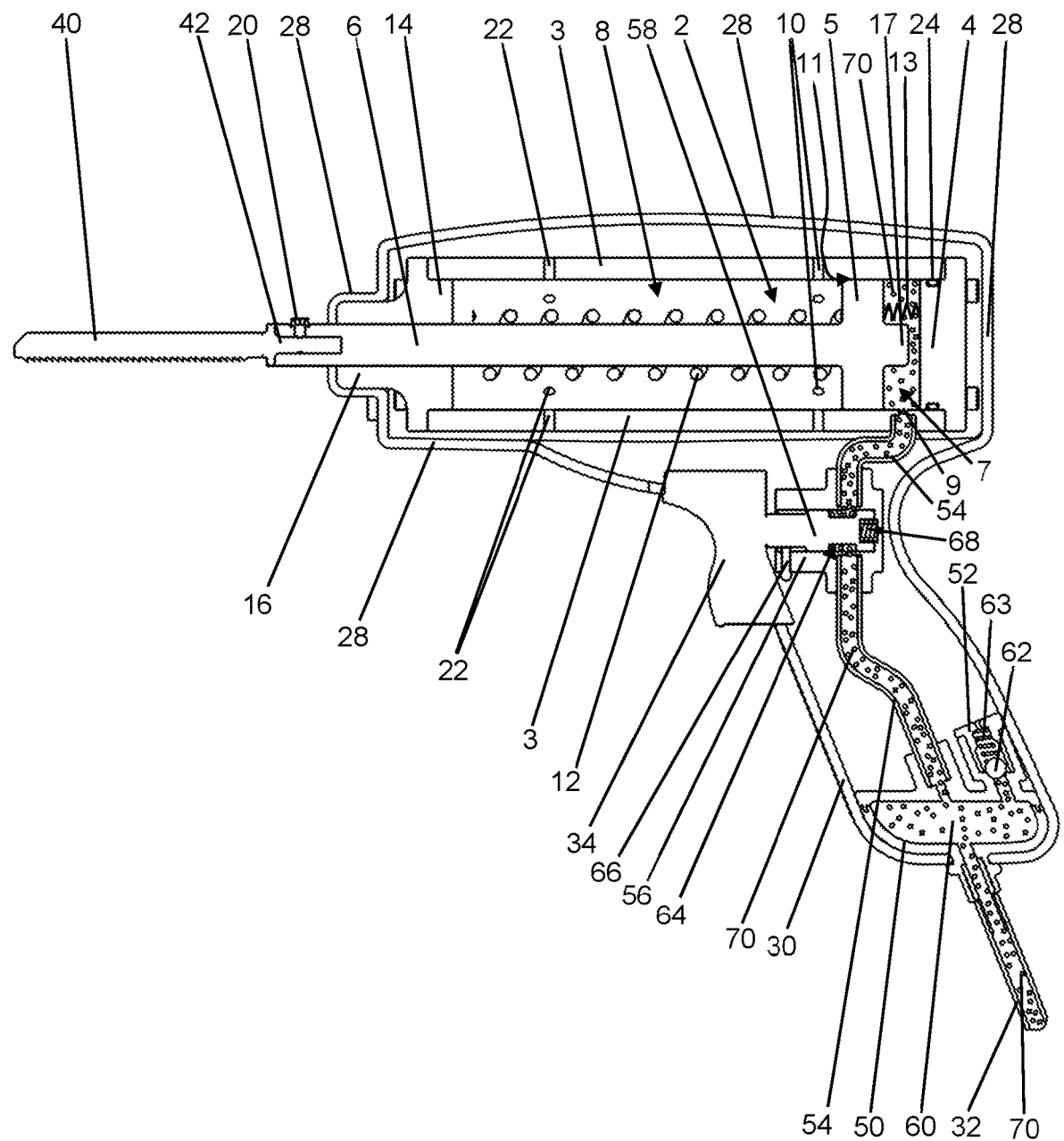
FIG. 9 is a schematic cross-sectional view of the surgical drive system according to FIGS. 2 to 8 with the compressed gas motor in operation during feed-in of compressed gas into the compressed gas motor.

The compressed gas 70 flows through the compressed gas line 54 and through the compressed gas port 9 into the back inner chamber 7 and begins to urge the plunger 5 in the hollow cylinder 2 towards the front closure 14. In this process, a small proportion of the compressed gas 70 forced into the back inner chamber 8 is pressed through the gap 11 between the plunger 5 and the cylinder jacket wall 3, such that a thin gas film forms between the plunger 5 and the cylinder jacket wall 3 on which the plunger 5 may slide in the hollow cylinder 2. This situation is shown in FIG. 9. The gap 11 is very small and therefore barely apparent in FIG. 9.

Figure 10:
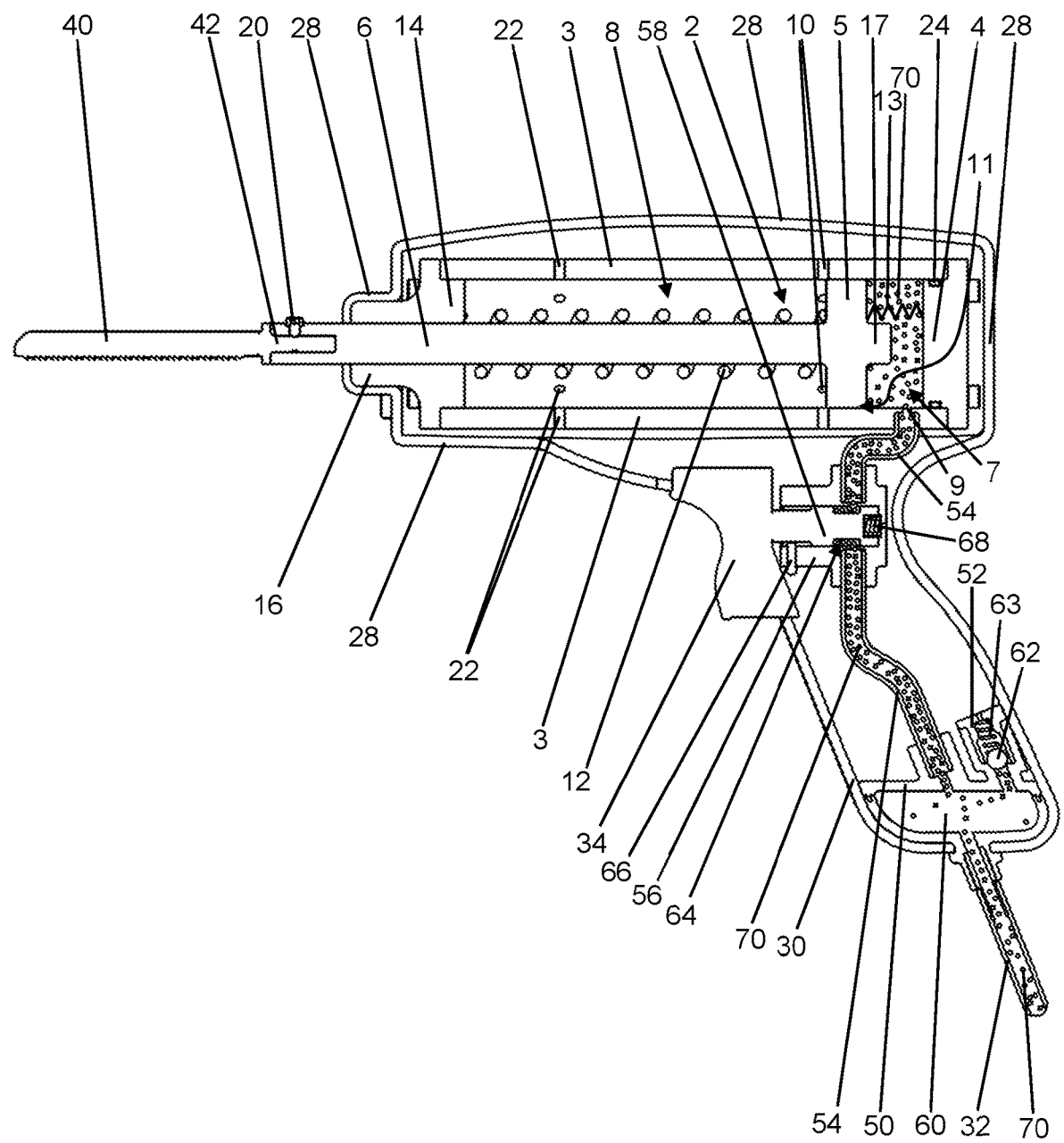
FIG. 10 is a schematic cross-sectional view of the surgical drive system according to FIGS. 2 to 9 with the compressed gas motor in operation during introduction of compressed gas into the compressed gas motor with the plunger in motion.

The compressed gas 70 is forced further into the back inner chamber 7, such that the plunger 5 is displaced towards the front closure 14 and the back inner chamber 7 is thereby enlarged. In the process, the compression spring 12, which rests on the plunger 5 and against the front closure 14, is compressed and tensioned. The plunger 5 urges the drive rod 6 out of the hollow cylinder 2 and in the process moves the saw 40 forward. This situation is shown in FIG. 10.

The plunger 5 is urged by the compressed gas 70 ever further toward the front closure 14 and in the process passes the ventilation openings 10. The back inner chamber 7 is thereby connected with the ventilation openings 10. Together, the ventilation openings 10 have a larger conduction cross-section than the compressed gas port 9. In this way, the compressed gas 70 escapes from the back inner chamber 7 toward the surrounding environment and subsequently out of the housing 28 through the vent openings 46. Due to the mass moment of inertia of the plunger 5, the drive rod 6, the spacer 17 and the saw 40, the plunger 5 overshoots and the ventilation openings 10 are fully opened. The pressure in the back inner chamber 7 reduces, as more compressed air 70 escapes from the back inner chamber 7 than can be replenished through the compressed gas port 9. This situation is shown in FIG. 11.

As the pressure in the back inner chamber 7 eases, the tensioned compression spring 12 accelerates the plunger 5 toward the rear closure 4. As it moves backward, the drive rod 6 with the saw 40 is also moved backward. The plunger 5 passes the ventilation openings 10 and is urged toward the rear closure until inflowing compressed gas 70 builds up a sufficiently high gas pressure in the back inner chamber 7 again that the movement is once again reversed. This situation is shown in FIG. 9.

The compressed gas motor 1 and the surgical drive system run while the valve element remains open. The plunger 5 and the drive rod 6 oscillate. In the process, the saw 40 is also moved in a linearly oscillating manner and may be used for example to saw bone.

In addition to the saw 40, the surgical drive system may also be used for other purposes, wherein the method remains virtually unchanged.

FIGS. 12 and 13 show the surgical drive system connected with a lavage attachment 72 instead of the saw 40. The lavage attachment 72 includes a holder 74, which is fastened on the surgical drive system with a fastener 76 in the form of a screw. To this end, the screw may have been or be screwed into the counter-fastening mechanism 44 in the form of a threaded bore. The holder 74 may be part of a housing 78 of the lavage attachment 72. An outer tube 80 extends out of the housing 78 and leads into a funnel 82.

Inside the funnel 82 a nozzle 86 is located through which a medical rinsing liquid may be expelled in spray bursts. A liquid feed line 88 and an extraction line 90 lead into the lavage attachment 72. The liquid feed line 88 is suitable for the intake of medical rinsing liquid into the lavage attachment 72. The used rinsing liquid and debrided body fluids and tissue residue can be extracted via the extraction line 90 and the funnel 82. To this end, the funnel 82 is connected to the extraction line 90 via the outer tube 80.

Inside the lavage attachment 70 a diaphragm pump is located which is designed to be driven by the drive rod 6 of the surgical drive system or of the compressed gas motor 1. To this end, the diaphragm pump includes a diaphragm 92, which is fastened in such a way in the housing 78 of the lavage attachment 72 that, on operation of the compressed gas motor 1, the drive rod 6 impacts repeatedly on the diaphragm 92. Rinsing liquid in a pump chamber 93 delimited by the diaphragm 92 at its rear end is pressed by the impact onto the diaphragm 92 through a one-way valve 96 and an inner tube 98 through the nozzle 86, where it is sprayed out. After resilient deformation of the diaphragm 92, the diaphragm 92 will retract again and thus increase the volume of the pump chamber 93. In the process, the one-way valve 96 closes and a second one-way valve 94, which is connected to the liquid feed line 88, opens and rinsing liquid can again flow into the pump chamber 93. The one-way valves 94, 96 are thus connected in opposite directions with the pump chamber 93, such that the one-way valve 94 permits only inflow into the pump chamber 93 while the one-way valve 96 permits only outflow out of the pump chamber 93. In this way, the surgical drive system can be used to drive the lavage attachment 72 to generate spray bursts.

As an alternative to the saw 40, other tools such as other saws 100 (FIG. 14), rasps 102 (FIG. 15) or brushes 104 (FIG. 16) may be connected to the fastening element 20 on the drive rod 6 or a liquid pump (see FIGS. 12 and 13) may also be connected and operated with the compressed gas motor 1, such that a spray burst of medical rinsing liquid is generated with the compressed gas motor 1 on each movement cycle of the drive rod 6. In this way, a lavage system according to the invention may be produced, which is depicted in FIGS. 12 and 13.

The features of the invention disclosed in the preceding description, as well as in the claims, figures and exemplary embodiments, may be essential both individually and in any combination for realizing the invention in its various embodiments. Although illustrated and described above with reference to certain specific embodiments and examples, the present disclosure is nevertheless not intended to be limited to the details shown. Rather, various modifications may be made in the details within the scope and range of equivalents of the claims and without departing from the spirit of the disclosure.

The invention claimed is:

1. A compressed gas motor comprising:
   a cylinder jacket wall defining a hollow cylinder with a front base and a rear base, the cylinder jacket wall having at least one ventilation opening;
   a rear closure at the rear base of the hollow cylinder;
   a drive rod projecting out of the hollow cylinder and having a front end;
   a plunger having a front end connected with the drive rod and being axially movable in the hollow cylinder, wherein the plunger divides the hollow cylinder in a non-gas-tight manner into a back inner chamber delimited by the plunger, the cylinder jacket wall, and the rear closure and a front inner chamber delimited by the plunger, the cylinder jacket wall, and the front base, wherein the at least one ventilation opening in the cylinder jacket wall is configured to connect the back inner chamber of the hollow cylinder with surrounding atmosphere for passage of gas during operation of the compressed gas motor and wherein the at least one ventilation opening periodically opens toward the back inner chamber during operation of the compressed gas motor by movement of the plunger;
   at least one compressed gas port connected into the back inner chamber of the hollow cylinder and configured to introduce a pressurized compressed gas into the back inner chamber; and
   at least one compression spring being arranged in the front inner chamber and resting during operation of the compressed gas motor at least temporarily against the front base of the hollow cylinder and/or at least one tension spring being arranged in the back inner chamber and connected with the plunger and with the rear closure of the hollow cylinder, wherein the at least one compression spring urges the plunger to such an extent toward the rear closure and/or the at least one tension spring draws the plunger to such an extent toward the rear closure that the back inner chamber of the hollow cylinder is closed relative to the at least one ventilation opening by the plunger and the back inner chamber is connected with the at least one compressed gas port when the same pressure prevails in the front inner chamber of the hollow cylinder and in the back inner chamber of the hollow cylinder.

2. The compressed gas motor according to claim 1, further comprising a front closure at the front base of the hollow cylinder, the front closure having a hole through which the drive rod passes, wherein the front inner chamber of the hollow cylinder is delimited by the plunger, the cylinder jacket wall, and the front closure.

3. The compressed gas motor according to claim 1, further comprising a compressed gas line connected with the at least one compressed gas port such that the compressed gas line is connected with the back inner chamber of the hollow cylinder for the passage of gas.

4. The compressed gas motor according to claim 1, wherein when the pressurized compressed gas is introduced through the at least one compressed gas port into the back inner chamber of the hollow cylinder, the plunger causes oscillating movement of the drive rod by periodic changing of an action of the compressed gas and of the surrounding atmosphere in the back inner chamber.

5. The compressed gas motor according to claim 1, wherein the at least one compression spring and/or the at least one tension spring is tensioned by the movement of the plunger towards the front base of the hollow cylinder driven by the compressed gas, and the plunger is urged by the tensioned at least one compression spring and/or the tensioned at least one tension spring toward the rear base when the back inner chamber is open to the surrounding atmosphere.

6. The compressed gas motor according to claim 1, wherein the plunger has a diameter of greater than or equal to 20 mm.

7. The compressed gas motor according to claim 1, further comprising a fastening element arranged at the front end of the drive rod and configured to engage a tool having a counter-fastening element matching the fastening element.

8. The compressed gas motor according to claim 1, wherein the cylinder jacket wall, the plunger, and the rear closure are made from a plastic material.

9. The compressed gas motor according to claim 1, wherein the at least one compression spring is a spiral spring that encloses the drive rod and the back inner chamber is devoid of the at least one tension spring.

10. The compressed gas motor according to claim 1, wherein the hollow cylinder has a cylinder axis and a cross-sectional area perpendicular to the cylinder axis and wherein the plunger and the cylinder jacket wall define a gap between the plunger and the cylinder jacket wall, the gap connecting the back inner chamber and the front inner chamber for the passage of gas and the gap having a cross-sectional area which is less than 1% of the cross-sectional area of the hollow cylinder perpendicular to the cylinder axis.

11. The compressed gas motor according to claim 10, wherein the gap is less than 50 μm wide and/or the gap is at least 0.5 μm wide.

12. The compressed gas motor according to claim 1, wherein the plunger has a stroke and a position of the at least one ventilation opening in the cylinder jacket wall determines the stroke of the plunger.

13. The compressed gas motor according to claim 1, wherein the plunger passes fully over the at least one ventilation opening during operation of the compressed gas motor or passes fully over at least one of the at least one ventilation openings.

14. A surgical drive system comprising:
  a compressed gas motor according to claim 1;
  a compressed gas line connected with the at least one compressed gas port and configured to be connected with a compressed gas reservoir; and
  a valve arranged in the compressed gas line and configured to interrupt the connection to the compressed gas reservoir and/or to adjust a pressure at the at least one compressed gas port.

15. The surgical drive system according to claim 14, further comprising a handle configured to be held in a hand and a trigger configured to actuate the valve using the same hand.

16. The surgical drive system according to claim 14 further comprising a sterile filter arranged in the compressed gas line.

17. A medical lavage system for debridement of soft tissue or bone tissue comprising:
  a tool for debriding soft tissue or bone tissue; and
  a compressed gas motor according to claim 1 or a surgical drive system according to claim 15, the compressed gas motor or the surgical drive system fastened to the tool.

18. A medical device for sawing, rasping, or brushing soft tissue or bone tissue comprising:
  a saw, a rasp, or a brush; and
  a compressed gas motor according to claim 1 or a surgical drive system according to claim 14, the drive rod of the compressed gas motor or of the surgical drive system fastened to the saw, the rasp, or the brush.

19. A method for operating a compressed gas motor in which a plunger oscillates in a linear and axial manner in a hollow cylinder and is connected to and drives a drive rod which projects out of the hollow cylinder, the method comprising the following chronological steps:
  (A) providing the compressed gas motor in an initial state in which the plunger delimits a back inner chamber of the hollow cylinder which is closed relative to surroundings of the compressed gas motor apart from at least one compressed gas port;
  (B) introducing a compressed gas into the back inner chamber of the hollow cylinder through the at least one compressed gas port;
  (C) pushing the plunger together with the drive rod toward a front end of the hollow cylinder with enlargement of the back inner chamber using the gas pressure of the compressed gas in the back inner chamber;
  (D) tensioning at least one compression spring and/or at least one tension spring by movement of the plunger;
  (E) opening at least one ventilation opening in a cylinder jacket wall of the hollow cylinder to the back inner chamber by the movement of the plunger, wherein the at least one ventilation opening is opened directly into the back inner chamber;
  (F) flowing the compressed gas out of the back inner chamber through the at least one ventilation opening;
  (G) returning the plunger by application of a force of the at least one compression spring and/or of the at least one tension spring to the plunger; and
  (H) closing the at least one ventilation opening relative to the back inner chamber through the movement of the plunger;
  wherein the method further comprising the step of providing a film of the compressed gas which flows through a gap between the plunger and an internal wall of the hollow cylinder, the plunger sliding in the hollow cylinder on the gas film.

20. The method according to claim 19, further comprising the step of driving a tool or a pump by movement of the drive rod or the plunger.

21. The method according to claim 19, wherein the compressed gas motor comprises:
  the cylinder jacket wall defining the hollow cylinder with a front base and a rear base;
  a rear closure at the rear base of the hollow cylinder;
  the drive rod projecting out of the hollow cylinder and having a front end;
  the plunger having a front end connected with the drive rod and being axially movable in the hollow cylinder, wherein the plunger divides the hollow cylinder into a back inner chamber delimited by the plunger, the cylinder jacket wall, and the rear closure and a front inner chamber delimited by the plunger, the cylinder jacket wall, and the front base, wherein the at least one ventilation opening in the cylinder jacket wall is configured to connect the back inner chamber of the hollow cylinder with surrounding atmosphere for passage of gas during operation of the compressed gas motor and wherein the at least one ventilation opening periodically opens toward the back inner chamber during operation of the compressed gas motor by movement of the plunger;
  the at least one compressed gas port connected into the back inner chamber of the hollow cylinder and configured to introduce a pressurized compressed gas into the back inner chamber; and
  the at least one compression spring being arranged in the front inner chamber and resting during operation of the compressed gas motor at least temporarily against the front base of the hollow cylinder and/or the at least one tension spring being arranged in the back inner chamber and connected with the plunger and with the rear closure of the hollow cylinder, wherein the at least one compression spring urges the plunger to such an extent toward the rear closure and/or the at least one tension spring draws the plunger to such an extent toward the rear closure that the back inner chamber of the hollow cylinder is closed relative to the at least one ventilation opening by the plunger and the back inner chamber is connected with the at least one compressed gas port when the same pressure prevails in the front inner chamber of the hollow cylinder and in the back inner chamber of the hollow cylinder.

22. The method according to claim 19, wherein the method is carried out with a surgical drive system comprising the compressed gas motor, the compressed gas motor comprising:

the cylinder jacket wall defining the hollow cylinder with a front base and a rear base;
a rear closure at the rear base of the hollow cylinder;
the drive rod projecting out of the hollow cylinder and having a front end;
the plunger having a front end connected with the drive rod and being axially movable in the hollow cylinder, wherein the plunger divides the hollow cylinder into a back inner chamber delimited by the plunger, the cylinder jacket wall, and the rear closure and a front inner chamber delimited by the plunger, the cylinder jacket wall, and the front base, wherein the at least one ventilation opening in the cylinder jacket wall is configured to connect the back inner chamber of the hollow cylinder with surrounding atmosphere for passage of gas during operation of the compressed gas motor and wherein the at least one ventilation opening periodically opens toward the back inner chamber during operation of the compressed gas motor by movement of the plunger;
the at least one compressed gas port connected into the back inner chamber of the hollow cylinder and configured to introduce a pressurized compressed gas into the back inner chamber; and
the at least one compression spring being arranged in the front inner chamber and resting during operation of the compressed gas motor at least temporarily against the front base of the hollow cylinder and/or the at least one tension spring being arranged in the back inner chamber and connected with the plunger and with the rear closure of the hollow cylinder, wherein the at least one compression spring urges the plunger to such an extent toward the rear closure and/or the at least one tension spring draws the plunger to such an extent toward the rear closure that the back inner chamber of the hollow cylinder is closed relative to the at least one ventilation opening by the plunger and the back inner chamber is connected with the at least one compressed gas port when the same pressure prevails in the front inner chamber of the hollow cylinder and in the back inner chamber of the hollow cylinder;
the surgical drive system further comprising a compressed gas line connected with the at least one compressed gas port and configured to be connected with a compressed gas reservoir;
and a valve arranged in the compressed gas line and configured to interrupt the connection to the compressed gas reservoir and/or to adjust a pressure at the at least one compressed gas port.

23. The method according to claim 19, wherein the method is carried out with a lavage system comprising:
a tool for debriding soft tissue or bone tissue, and the compressed gas motor or a tool for debriding soft tissue or bone tissue, and a surgical drive system, the compressed gas motor comprising:
the cylinder jacket wall defining the hollow cylinder with a front base and a rear base;
a rear closure at the rear base of the hollow cylinder;
the drive rod projecting out of the hollow cylinder and having a front end;
the plunger having a front end connected with the drive rod and being axially movable in the hollow cylinder, wherein the plunger divides the hollow cylinder into a back inner chamber delimited by the plunger, the cylinder jacket wall, and the rear closure and a front inner chamber delimited by the plunger, the cylinder jacket wall, and the front base, wherein the at least one ventilation opening in the cylinder jacket wall is configured to connect the back inner chamber of the hollow cylinder with surrounding atmosphere for passage of gas during operation of the compressed gas motor and wherein the at least one ventilation opening periodically opens toward the back inner chamber during operation of the compressed gas motor by movement of the plunger;
the at least one compressed gas port connected into the back inner chamber of the hollow cylinder and configured to introduce a pressurized compressed gas into the back inner chamber; and
the at least one compression spring being arranged in the front inner chamber and resting during operation of the compressed gas motor at least temporarily against the front base of the hollow cylinder and/or the at least one tension spring being arranged in the back inner chamber and connected with the plunger and with the rear closure of the hollow cylinder, wherein the at least one compression spring urges the plunger to such an extent toward the rear closure and/or the at least one tension spring draws the plunger to such an extent toward the rear closure that the back inner chamber of the hollow cylinder is closed relative to the at least one ventilation opening by the plunger and the back inner chamber is connected with the at least one compressed gas port when the same pressure prevails in the front inner chamber of the hollow cylinder and in the back inner chamber of the hollow cylinder;
the surgical drive system comprising the compressed gas motor and further comprising a compressed gas line connected with the at least one compressed gas port and configured to be connected with a compressed gas reservoir; and a valve arranged in the compressed gas line and configured to interrupt the connection to the compressed gas reservoir and/or to adjust a pressure at the at least one compressed gas port, wherein the drive rod of the compressed gas motor or the surgical drive system is fastened to the tool.

24. The method according to claim 19, wherein the method is carried out with a medical device for sawing, rasping, or brushing soft tissue or bone tissue, the medical device comprising:
a saw, a rasp, or a brush, and the compressed gas motor or a saw, a rasp, or a brush, and a surgical drive system, the compressed gas motor comprising:
the cylinder jacket wall defining the hollow cylinder with a front base and a rear base;
a rear closure at the rear base of the hollow cylinder;
the drive rod projecting out of the hollow cylinder and having a front end;
the plunger having a front end connected with the drive rod and being axially movable in the hollow cylinder, wherein the plunger divides the hollow cylinder into a back inner chamber delimited by the plunger, the cylinder jacket wall, and the rear closure and a front inner chamber delimited by the plunger, the cylinder jacket wall, and the front base, wherein the at least one ventilation opening in the cylinder jacket wall is configured to connect the back inner chamber of the hollow cylinder with surrounding atmosphere for passage of gas during operation of the compressed gas motor and wherein the at least one ventilation opening periodically opens toward the back inner chamber during operation of the compressed gas motor by movement of the plunger;

the at least one compressed gas port connected into the back inner chamber of the hollow cylinder and configured to introduce a pressurized compressed gas into the back inner chamber; and the at least one compression spring being arranged in the front inner chamber and resting during operation of the compressed gas motor at least temporarily against the front base of the hollow cylinder and/or the at least one tension spring being arranged in the back inner chamber and connected with the plunger and with the rear closure of the hollow cylinder, wherein the at least one compression spring urges the plunger to such an extent toward the rear closure and/or the at least one tension spring draws the plunger to such an extent toward the rear closure that the back inner chamber of the hollow cylinder is closed relative to the at least one ventilation opening by the plunger and the back inner chamber is connected with the at least one compressed gas port when the same pressure prevails in the front inner chamber of the hollow cylinder and in the back inner chamber of the hollow cylinder;

the surgical drive system comprising the compressed gas motor and further comprising a compressed gas line connected with the at least one compressed gas port and configured to be connected with a compressed gas reservoir; and a valve arranged in the compressed gas line and configured to interrupt the connection to the compressed gas reservoir and/or to adjust a pressure at the at least one compressed gas port;

wherein the drive rod of the compressed gas motor or of the surgical drive system is fastened to the saw, the rasp, or the brush.

* * * * *